United States Patent [19]
Schwender et al.

[11] Patent Number: 6,037,324
[45] Date of Patent: Mar. 14, 2000

[54] INHIBITORS OF MADCAM-1-MEDIATED INTERACTIONS AND METHODS OF USE THEREFOR

[75] Inventors: Charles F. Schwender, Dover; Hitesh N. Shroff, Bedford, both of Mass.

[73] Assignee: LeukoSite, Inc., Cambridge, Mass.

[21] Appl. No.: 08/582,740

[22] Filed: Jan. 4, 1996

[51] Int. Cl.$^7$ .......................... A61K 38/00; A61K 38/06; A61K 38/07

[52] U.S. Cl. ............................. 514/18; 514/19; 530/300; 530/331

[58] Field of Search ................................... 530/331, 317; 514/18, 19, 11

[56] References Cited

U.S. PATENT DOCUMENTS

| | | | |
|---|---|---|---|
| 5,134,121 | 7/1992 | Mobley | 514/14 |
| 5,192,746 | 3/1993 | Lobl et al. | 514/11 |
| 5,358,934 | 10/1994 | Borovsky | 514/17 |
| 5,436,221 | 7/1995 | Kitaguchi | 514/12 |
| 5,510,332 | 4/1996 | Kogan et al. | 514/14 |
| 5,728,677 | 3/1998 | Wallner et al. | 514/12 |
| 5,728,802 | 3/1998 | Barrett et al. | 530/324 |
| 5,756,449 | 5/1998 | Andersen et al. | 514/8 |

FOREIGN PATENT DOCUMENTS

| | | |
|---|---|---|
| WO 92/00995 | 1/1992 | WIPO . |
| 93/08823 | 5/1992 | WIPO . |
| 9306128 | 4/1993 | WIPO . |
| WO 93/12809 A1 | 7/1993 | WIPO . |
| WO 93/21206 | 10/1993 | WIPO . |
| WO 94/15958 | 7/1994 | WIPO . |
| WO 95/15973 | 6/1995 | WIPO . |
| WO 96/00581 | 1/1996 | WIPO . |
| WO 96/01644 | 1/1996 | WIPO . |
| WO 96/06108 | 2/1996 | WIPO . |
| WO 97/03094 | 1/1997 | WIPO . |

OTHER PUBLICATIONS

Martens et al. J. Biol. Chem., 270: 21129–21136, Oct. 1995.
U.S.S.N. 08/498,237 entitles Cell Adhesion Inhibitors, by Lin et al., filed on Jul. 11, 1995.
Shroff, H. N., et al., "Small Peptide Inhibitors of $\alpha_4\beta_7$ Mediated MAdCAM–1 Adhesion to Lymphocytes," *Bioorganic & Medicinal Chemistry Letters*, 6(21):2495–2500 (1996).
Komoriya, A. et al., "The Minimal Essential Sequence for a Major Cell Type–Specific Adhesion Site (CS1) within the Alternatively Spliced Type III Connecting Segment Domain of Fibronectin is Leucine–Aspartic Acid–Valine," *The Journal of Biological Chemistry*, 226(23):15075–15079 (1991).
Yongjun Duan and R. A. Laursen, "Protease Substrate Specificity Mapping Using Membrane–Bound Peptides," *Analytical Biochemistry*, 216:431 438 (1994).
van Amerongen, A. et al., "Peptide Reactive with a Transmission–Blocking Monoclonal Antibody Against *Plasmodium–falciparum* Pfs25: 2000–Fold Affinity Increase by PEPSCAN–Based Amino Acid Substitutions," *Peptide Research*, 5(5):269–274 (1992).

Stura, E. A. et al., "Crystallization of an Intact Monoclonal Antibody (4B7) Against *Plasmodium Falciparum Marlaria* with Peptides from the Pfs25 Protein Antigen," *Acta. Cryst.* D50:556–562 (1994).
Stura, E. A. et al., "Crystallization Sequence and Preliminary Crystallographic Data for Transmission–Blocking Anti–Malaria Fab 4B7 with Cyclic Peptides from the Pfs25 Protein of *P. Falciparum*," *Acta. Cryst.* D50:535–542 (1994).
Stura, E. A. et al., "Crystallization of Neutralizing Malaria Immunoglobulin with Linear and Cyclic Peptides," *Pept. Chem. Struct. Biol., Proc. Am. Pept. Symp. 13th*, Editor, Hodges, Robert S. and Smith, John A., pp. 817–819 (1994).
Briskin, M. J. et al., "MAdCAM–1 has Homology to Immunoglobulin and Mucin–Like Adhesion Receptors and to lgA1," *Nature*, 363:461–464 (Jun. 3, 1993).
Wang, J. H., et al., "The Crystal Structure of an N–terminal Two–Domain Fragment of Vascular Cell Adhesion Molecule 1 (VCAM–1): A Cyclic Peptide Based on the Domain 1 C–D Loop can Inhibit VCAM–1–$\alpha$4 Integrin Interaction," *Proc. Natl. Acad. Sci. USA*, 92:5714–5718 (Jun. 1995).
Vonderheide, R. H. et al., "Residues within a Conserved Amino Acid Motif of Domains 1 and 4 of VCAM–1 are Required for Binding to VLA-4," *The Journal of Cell Biology*, 125(1):215–222 (Apr. 1994).
Osborn, L. et al., "Arrangement of Domains, and Amino Acid Residues Required for Binding of Vascular Cell Adhesion Molecule–1 to its Counter–Receptor VLA–4 ($\alpha_4\beta_1$)," *The Journal of Cell Biology*, 124(4):601–608 (Feb. 1994).
Priskin, M. et al., "Structural and Functional Analysis of the Mucosal Vascular Addressin MADCAM–1," *Clinical Immunology and Immunopathology*, 76(1) (part 2) = S85, 8th International Congress of Mucosal Immunology, San Diego, California, Jul. 17 to Jul 20, 1995.
Renz, M. E., et al., "Structural Requirements for Adhesion of Soluble Recombinant Murine Vascular Cell Adhesion Molecule–1 to $\alpha 4\beta 1$," *The Journal of Cell Biology*, 125(6):1395–1406 (Jun. 1994).
Briskin, M., "In Vitro and In Vivo Analysis of MAD-CAM–1/$\alpha 4\beta 7$ Adhesive Interactions: Implications for Involvement in Inflammatory Bowel Disease," International Symposium, Molecular Mechanisms of Inflammation, Sep. 6–9, 1995.
Wayner, E. A., "Activation–Dependent Recognition by Hematopoietic Cells of the LDV Sequence in the V Region of Fibronectin," *The Journal of Cell Biology*, 116(2):489–497 (Jan. 1992).

*Primary Examiner*—Cecilia Tsang
*Assistant Examiner*—Michael Borin
*Attorney, Agent, or Firm*—Hamilton, Brook, Smith & Reynolds, P.C.

[57] ABSTRACT

The present invention provides novel compounds comprising peptide sequences which mimic the conserved amino acid motif LDTSL and which have groups bonded to the N- and C-termini. Also provided are methods of inhibiting the interaction of a cell bearing a ligand of MAdCAM-1, such as human $\alpha 4\beta 7$, with MAdCAM-1 or a portion thereof (e.g., the extracellular domain), comprising contacting the cell with a compound of the present invention.

32 Claims, 4 Drawing Sheets

```
       BamHI
       GGA TTC ATG GAA TCC ATC CTG----------------------------------
               M   E   S   I   L

Signal Peptide of MAdCAM-1 . . .

Complete Extracellular Domain of Murine MAdCAM-1
       ----------------------------//----------------------------------

BamHI
       ---CCG AAT TCC TCC TCC ACC GGA TCC GCT GAT GCT GCA CCA ----------
            P   N   S   S   S   T   G   S   A   D   A   A   P . . .
                                              Murine $C_\kappa$ . . .
```

FIG. 3

```
ATGGATTTCGGACTGGCCCTCCTGCTGGCGGGGCTTCTGGGGCTCCTCCTCGGCCAGTCCCTCCAGGTGAAGCCCCTGCA  80
 M  D  F  G  L  A  L  L  L  A  G  L  L  G  L  L  L  G  Q  S  L  Q  V  K  P  L  Q
GGTGGAGCCCCCGGAGCCGGTGGTGGCCGTGGCCTTGGGCGCCTCGCGCCAGCTCACCTGCCGCCTGGCCTGCGCGGACC  160
 V  E  P  P  E  P  V  V  A  V  A  L  G  A  S  R  Q  L  T [C] R  L  A [C] A  D
GCGGGGCCTCGGTGCAGTGGCGGGGCCTGGACACCAGCCTGGGCGCGGTGCAGTCGGACACGGGCCGCAGCGTCCTCACC  240
 R  G  A  S  V  Q  W  R  G  L  D  T  S  L  G  A  V  Q  S  D  T  G  R  S  V  L  T
GTGCGCAACGCCTCGCTGTCGGCGGCCGGGACCCGCGTGTGCGTGGGCTCCTGCGGGGGCCGCACCTTCCAGCACACCGT  320
 V  R [N  A  S] L  S  A  A  G  T  R  V [C] V  G  S [C] G  G  R  T  F  Q  H  T  V
GCAGCTCCTTGTGTACGCCTTCCCGGACCAGCTGACCGTCTCCCCAGCAGCCCTGGTGCCTGGTGACCCGGAGGTGGCCT  400
 Q  L  L  V  Y  A  F  P  D  Q  L  T  V  S  P  A  A  L  V  P  G  D  P  E  V  A
GTACGGCCCACAAAGTCACGCCCGTGGACCCCAACGCGCTCTCCTTCTCCCTGCTCGTCGGGGGCCAGGAACTGGAGGGG  480
[C] T  A  H  K  V  T  P  V  D  P  N  A  L  S  F  S  L  L  V  G  G  Q  E  L  E  G
GCGCAAGCCCTGGGCCCGGAGGTGCAGGAGGAGGAGGAGGAGCCCCAGGGGGACGAGGACGTGCTGTTCAGGGTGACAGA  560
 A  Q  A  L  G  P  E  V  Q  E  E  E  E  E  P  Q  G  D  E  D  V  L  F  R  V  T  E
GCGCTGGCGGCTGCCGCCCCTGGGGACCCCTGTCCCGCCCGCCCTCTACTGCCAGGCCACGATGAGGCTGCCCTGGCTTGG  640
 R  W  R  L  P  P  L  G  T  P  V  P  P  A  L  Y [C] Q  A  T  M  R  L  P  G  L
AGCTCAGCCACCGCCAGGCCATCCCCGTCCTGCACAGCCCGACCTCCCCGGAGCCTCCCGACACCACCTCCCCGGAGCCT  720
 E  L  S  H  R  Q  A  I  P  V  L  H  S  P  T  S  P  E  P  P  D  T  T  S  P  E  P
CCCAACACCACCTCCCCGGAGTCTCCCGACACCACCTCCCCGGAGTCTCCCGACACCACCTCCCAGGAGCCTCCCGACAC  800
 P [N  T  T] S  P  E  S  P  D  T  T  S  P  E  S  P  D  T  T  S  Q  E  P  P  D  T
CACCTCCCAGGAGCCTCCCGACACCACCTCCCCAGGAGCCTCCCGACACCACCTCCCCGGAGCCTCCCGACAAGACCTCCC  880
 T  S  Q  E  P  P  D  T  T  S  Q  E  P  P  D  T  T  S  P  E  P  P  D  K  T  S
CGGAGCCGGCCCCCAGCAGGGCTCCACACACACCCCCAGGAGCCCAGGCTCCACCAGGACTCGCCGCCCTGAGATCTCC  960
 P  E  P  A  P  Q  Q  G  S  T  H  T  P  R  S  P  G  S  T  R  T  R  R  P  E  I  S
CAGGCTGGGCCCACGCAGGGAGAAGTGATCCCAACAGGCTCGTCCAAACCTGCGGGTGACCAGCTGCCCGCGGCTCTGTG  1040
 Q  A  G  P  T  Q  G  E  V  I  P  T  G  S  S  K  P  A  G  D  Q  L  P  A  A  L  W
GACCAGCAGTGCGGTGCTGGGACTGCTGCTCCTGGCCTTGCCCACGTATCACCTCTGGAAACGCTGCCGGCACCTGGCTG  1120
 T  S  S  A  V  L  G  L  L  L  L  A  L  P  T  Y  H  L  W  K  R  C  R  H  L  A
AGGACGACACCCACCCACCAGCTTCTCTGAGGCTTCTGCCCCAGGTGTCGGCCTGGGCTGGGTTAAGGGGGACCGGCCAG  1200
 E  D  D  T  H  P  P  A  S  L  R  L  L  P  Q  V  S  A  W  A  G  L  R  G  T  G  Q
GTCGGGATCAGCCCCTCCTGAGTGGCCAGCCTTTCCCCCTGTGAAAGCAAAATAGCTTGGACCCCTTCAAGTTGAGAACT  1280
 V  G  I  S  P  S
GGTCAGGGCAAACCTGCCTCCCATTCTACTCAAAGTCATCCCTCTGCTCACAGAGATGGATGCATGTTCTGATTGCCTCT  1360

TTGGAGAAGCTCATCAGAAACTCAAAAGAAGGCCACTGTTTGTCTCACCTACCCATGACCTGAAGCCCCTCCCTGAGTGG  1440

TCCCCACCTTTCTGGACGGAACCACGTACTTTTTACATACATTGATTCATGTCTCACGTCTCCCTAAAAATGCGTAAGAC  1520

CAAGCTGTGCCCTGACCACCCTGGGCCCCTGTCGTCAGGACCTCCTGAGGCTTTGGCAAATAAACCTCCTAAAATGATAA  1600

AAAAAAAAAAAAAAAAAAAAAAAA  1624
```

FIG. 4

```
ATGGATTTCGGACTGGCCCTCCTGCTGGCGGGGCTTCTGGGGCTCCTCCTCGGCCAGTCCCTCCAGGTGAAGCCCCTGCA  80
 M  D  F  G  L  A  L  L  L  A  G  L  L  G  L  L  L  G  Q  S  L  Q  V  K  P  L  Q
GGTGGAGCCCCCGGAGCCGGTGGTGGCCGTGGCCTTGGGCGCCTCGCGCCAGCTCACCTGCCGCCTGGCCTGCGCGGACC 160
 V  E  P  P  E  P  V  V  A  V  A  L  G  A  S  R  Q  L  T [C] R  L  A [C] A  D
GCGGGGCCTCGGTGCAGTGGCGGGGCCTGGACACCAGCCTGGGCGCGGTGCAGTCGGACACGGGCCGCAGCGTCCTCACC 240
 R  G  A  S  V  Q  W  R  G  L  D  T  S  L  G  A  V  Q  S  D  T  G  R  S  V  L  T
GTGCGCAACGCCTCGCTGTCGGCGGCCGGGACCCGCGTGTGCGTGGGCTCCTGCGGGGGCCGCACCTTCCAGCACACCGT 320
 V  R [N  A  S] L  S  A  A  G  T  R  V [C] V  G  S [C] G  G  R  T  F  Q  H  T  V
GCAGCTCCTTGTGTACGCCTTCCCGGACCAGCTGACCGTCTCCCCAGCAGCCCTGGTGCCTGGTGACCCGGAGGTGGCCT 400
 Q  L  L  V  Y  A  F  P  D  Q  L  T  V  S  P  A  A  L  V  P  G  D  P  E  V  A
GTACGGCCCACAAAGTCACGCCCGTGGACCCCAACGCGCTCTCCTTCTCCCTGCTCGTCGGGGGCCAGGAACTGGAGGGG 480
[C] T  A  H  K  V  T  P  V  D  P  N  A  L  S  F  S  L  L  V  G  G  Q  E  L  E  G
GCGCAAGCCCTGGGCCCGGAGGTGCAGGAGGAGGAGGAGGAGCCCCAGGGGGACGAGGACGTGCTGTTCAGGGTGACAGA 560
 A  Q  A  L  G  P  E  V  Q  E  E  E  E  E  P  Q  G  D  E  D  V  L  F  R  V  T  E
GCGCTGGCGGCTGCCGCCCCTGGGGACCCCTGTCCCGCCCGCCCTCTACTGCCAGGCCACGATGAGGCTGCCTGGCTTGG 640
 R  W  R  L  P  P  L  G  T  P  V  P  P  A  L  Y [C] Q  A  T  M  R  L  P  G  L
AGCTCAGCCACCGCCAGGCCATCCCCGTCCTGCACAGCCCGACCTCCCCGGAGCCTCCCGACACCACCTCCCCGGAGTCT 720
 E  L  S  H  R  Q  A  I  P  V  L  H  S  P  T  S  P  E  P  P  D  T  T  S  P  E  S
CCCGACACCACCTCCCCGGAGTCTCCCGACACCACCTCCCCAGGAGCCTCCCGACACCACCTCCCCGGAGCCTCCCGACAA 800
 P  D  T  T  S  P  E  S  P  D  T  T  S  Q  E  P  P  D  T  T  S  P  E  P  P  D  K
GACCTCCCCGGAGCCCGCCCCCCAGCAGGGCTCCACACACACCCCCAGGAGCCCAGGCTCCACCAGGACTCGCCGCCCTG 880
 T  S  P  E  P  A  P  Q  Q  G  S  T  H  T  P  R  S  P  G  S  T  R  T  R  R  P
AGATCTCCCAGGCTGGGCCCACGCAGGGAGAAGTGATCCCAACAGGCTCGTCCAAACCTGCGGGTGACCAGCTGCCCGCG 960
 E  I  S  Q  A  G  P  T  Q  G  E  V  I  P  T  G  S  S  K  P  A  G  D  Q  L  P  A
GCTCTGTGGACCAGCAGTGCGGTGCTGGGACTGCTGCTCCTGGCCTTGCCCACCTATCACCTCTGGAAACGCTGCCGGCA 1040
 A  L  W  T  S  S  A  V  L  G  L  L  L  L  A  L  P  T  Y  H  L  W  K  R  C  R  H
CCTGGCTGAGGACGACACCCCACCCACCAGCTTCTCTGAGGCTTCTGCCCCAGGTGTCGGCCTGGGCTGGGTTAAGGGGGA 1120
 L  A  E  D  D  T  H  P  P  A  S  L  R  L  L  P  Q  V  S  A  W  A  G  L  R  G
CCGGCCAGGTCGGGATCAGCCCCTCCTGAGTGGCCAGCCTTTCCCCCTGTGAAAGCAAAATAGCTTGGACCCCTTCAAGT 1200
 T  G  Q  V  G  I  S  P  S
TGAGAACTGGTCAGGGCAAACCTGCCTCCCATTCTACTCAAAGTCATCCCTCTGTTCACAGAGATGGATGCATGTTCTGA 1280

TTGCCTCTTTGGAGAAGCTCATCAGAAACTCAAAAGAAGGCCACTGTTTGTCTCACCTACCCATGACCTGAAGCCCCTCC 1360

CTGAGTGGTCCCCACCTTTCTGGACGGAACCACGTACTTTTTACATACATTGATTCATGTCTCACGTCTCCCTAAAAATG 1440

CGTAAGACCAAGCTGTGCCCTGACCACCCTGGGCCCCTGTCGTCAGGACCTCCTGAGGCTTTGGCAAATAAACCTCCTAA 1520

AATGAAAAAAAAAAAAAAA 1539
```

FIG. 5

INHIBITORS OF MADCAM-1-MEDIATED INTERACTIONS AND METHODS OF USE THEREFOR

GOVERNMENT SUPPORT

Work described herein was supported in whole or in part by Government Grant No. 43DK8498301. The government may have certain rights in this invention.

BACKGROUND OF THE INVENTION

Lymphocyte homing from the circulation to the lymphoid tissues and migration to sites of inflammation is regulated by interaction with receptors expressed in postcapillary venules, including high endothelial venules (HEV) found in secondary lymphoid tissues (e.g., mesenteric lymph nodes, Peyer's Patches (PP)) (Bevilacqua, M. P., *Annu. Rev. Immunol.*, 11:767–804 (1993); Butcher, E. C., *Cell*, 67: 1033–1036 (1991); Picker, L. J., et al., *Annu. Rev. Immunol.*, 10:561–591 (1992); and Springer, T. A., *Cell*, 76: 301–314 (1994)). These interactions are tissue specific in nature.

Inflammation (e.g., chronic inflammation) is characterized by infiltration of the affected tissue by leukocytes, such as lymphocytes, lymphoblasts, and mononuclear phagocytes. The remarkable selectivity by which leukocytes preferentially migrate to various tissues during both normal circulation and inflammation results from a series of adhesive and activating events involving multiple receptor-ligand interactions as proposed by Butcher and others (Butcher, E. C., *Cell*, 67: 1033–1036 (1991); vonAdrian, U. H., et al., *Proc. Natl. Acad. Sci. USA*, 88:7538 (1991); Mayadas, T. N., et al., *Cell*, 74:541 (1993); (Springer, T. A., *Cell*, 76:301 (1994)). As an initial step, there is a transient, rolling interaction between leukocytes and endothelium, which results from the interaction of selectins (and by α4 integrins in some instances) with their carbohydrate ligands. This interaction, which is characterized by rolling in the direction of flow, can be assessed by known methods (Lawrence, M. B. and T. A. Springer, *Cell*, 65:859 (1991); WO 92/21746, Springer et al., (Dec. 10, 1992)). This is followed by activation events mediated by chemoattractants such as chemokines and their receptors, which cause activation of integrin adhesiveness and influence the direction of migration of leukocytes through vascular walls. Such secondary signals in turn trigger the firm adhesion of leukocytes to endothelium via leukocyte integrins and their endothelial ligands (Ig-like receptors and the ECM), and subsequent transendothelial migration from the circulation across the vascular endothelium.

In secondary lymphoid tissues, such as Peyer's patches (PPs) and lymph nodes (e.g., peripheral lymph nodes (PLN)), leukocyte trafficking and homing is regulated by interactions of homing receptors on the surface of leukocytes with endothelial cells lining the post-capillary venules, notably high endothelial venules (HEV) (Gowans, J. L. and E. J. Knight, *Proc. R. Soc. Lond.*, 159:257 (1964)). Receptors termed vascular addressing, which are present on the endothelial cell surface and regulate the migration and subsequent extravasation of lymphocyte subsets. The vascular addressins show restricted patterns of expression and this tissue specific expression makes an important contribution to the specificity of leukocyte trafficking (Picker, L. J. and E. C. Butcher, *Annu. Rev. Immunol.*, 10:561–591 (1992); Berg, E. L., et al., *Cellular and molecular mechanisms of inflammation*, 2:111 (1991); Butcher, E. C., *Cell*, 67:1033–1036 (1991)).

Mucosal vascular addressin MAdCAM-1 (Mucosal Addressin Cell Adhesion Molecule-1) is an immunoglobulin superfamily adhesion receptor for lymphocytes, which is distinct from VCAM-1 and ICAM-1. MAdCAM-l was identified in the mouse as a ~60 kd glycoprotein which is selectively expressed at sites of lymphocyte extravasation. In particular, MAdCAM-1 expression was reported in vascular endothelial cells of mucosal tissues, including gut-associated tissues or lymphoid organs, such as Peyer's patches and venules of the lamina propria of the small and large intestine, and the lactating mammary gland, but not in peripheral lymph nodes. MAdCAM-1 is involved in lymphocyte binding to Peyer's Patches. (Streeter, P. R., et al., *Nature*, 331:41–46 (1988); Nakache, M., et al., *Nature*, 337: 179–181 (1989); Picker, L. J., et al., *Annu. Rev. Immunol.*, 10:561–591 (1992); Briskin, M. J., et al., *Nature*, 363:461 (1993); Berg, E. L., et al., *Nature*, 366:695–698 (1993); Berlin, C., et al., *Cell*, 74:185–195 (1993)). MAdCAM-1 can be induced in vitro by proinflammatory stimuli (Sikorski, E. E., et al., *J. Immunol.*, 151:5239–5250 (1993)). cDNA clones encoding murine and primate (e.g., human) MAdCAM-1 have been isolated and sequenced (Briskin, M. J. et al., *Nature*, 363: 461–464 (1993); and Briskin, M. J. et al., U.S. Ser. No. 08/523,004, filed Sep. 1, 1995, the teachings of both of which are incorporated herein by reference in their entirety).

MAdCAM-1 specifically binds the lymphocyte integrin α4β7 (also referred to as LPAM-1 (mouse), α4βp (mouse)), which is a lymphocyte homing receptor involved in homing to Peyer's patches (Berlin, C., et al., *Cell*, 80:413–422 (1994); Berlin, C., et al., *Cell*, 74:185–195 (1993); and Erle, D. J., et al., *J. Immunol.*, 153: 517–528 (1994)). In contrast to VCAM-1 and fibronectin, which interact with both α4β1 and α4β7 (Berlin, C., et al., *Cell*, 74: 185–195 (1993); Strauch, U. S., et al., *Int. Immunol.*, 6:263 (1994)), MAdCAM-1 is a selective ligand for α4β7 receptor.

Inflammatory bowel disease (IBD), such as ulcerative colitis and Crohn's disease, for example, can be a debilitating and progressive disease involving inflammation of the gastrointestinal tract. Affecting an estimated two million people in the United States alone, symptoms include abdominal pain, cramping, diarrhea and rectal bleeding. IBD treatments have included anti-inflammatory drugs (such as corticosteroids and sulfasalazine), immunosuppressive drugs (such as 6-mercaptopurine, cyclosporine and azathioprine) and surgery (such as, colectomy). Podolsky, *New Engl. J. Med.*, 325:928–937 (1991) and Podolsky, *New Engl. J. Med.*, 325:1008–1016 (1991). There is a need for inhibitors of MAdCAM-1 function to provide new therapies useful in the treatment of IBD and other diseases involving leukocyte infiltration of the gastrointestinal tract or other mucosal tissues.

SUMMARY OF THE INVENTION

As shown herein, the conserved amino acid motif LDTSL (SEQ ID NO:1) is involved in Mucosal Addressin Cell Adhesion Molecule-1 (hereinafter "MAdCAM-1") binding to MAdCAM-1 ligands, such as human α4β7. In addition, compounds containing this peptide sequence or truncated versions thereof, e.g., Asp-Thr and Leu-Asp-Thr, bind to α4β7 and can inhibit adhesion of leukocytes expressing α4β7 on the cell surface to MAdCAM-1. It has also been discovered that groups on the N- and C-termini of the peptide sequences enhance the binding of these compounds to α4β7 and are more potent inhibitors of interaction between MAdCAM-1 and its ligands. Accordingly, the present invention provides novel compounds comprising peptide sequences which mimic the conserved amino acid motif LDTSL (SEQ ID NO: 1) and which have groups bonded to the N- and C-termini.

Also provided are methods of inhibiting the interaction of a cell bearing a ligand of MAdCAM-1, including α4β7 integrins, with MAdCAM-1 or a portion thereof (e.g., the extracellular domain), comprising contacting the cell with a compound of the present invention. In one embodiment, the invention relates to a method of inhibiting the MAdCAM-mediated interaction of a first cell bearing an α4β7 integrin with MAdCAM, for example with a second cell bearing MAdCAM, comprising contacting the first cell with a compound of the present invention. In another embodiment, the invention relates to a method of treating an individual suffering from a disease associated with leukocyte recruitment to tissues (e.g., endothelium) expressing the molecule MAdCAM-1.

One embodiment of the present invention is a method of inhibiting the binding of a cell such as a leukocyte expressing a ligand for MAdCAM-1 on the cell surface (e.g. α4β7) to MAdCAM-1, for example to endothelial cells expressing MAdCAM-1 on the cell surface. The method comprises contacting the leukocytes with an effective amount of an inhibitor represented by Structural Formula (I):

Y is a pentapeptide $[AA]_1$-$[AA]_2$-$[AA]_3$-$[AA]_4$-$[AA]_5$.

$[AA]_1$ is selected from the group consisting of leucine, valine, isoleucine, alanine, phenylalanine, glycine, N-methylleucine, serine, threonine, ornithine, cysteine, aspartic acid, glutamic acid and lysine.

$[AA]_2$ is selected from the group consisting of aspartic acid, glutamic acid, phenylalanine and tyrosine.

$[AA]_3$ is selected from the group consisting of threonine, serine, valine, proline and 4-hydroxyproline.

$[AA]_4$ is selected from the group consisting of serine, cysteine, aspartic acid, glutamic acid, proline, 4-hydroxyproline, threonine, valine, isoleucine, alanine, glycine, ornithine and lysine.

$[AA]_5$ is selected from the group consisting of leucine, valine, isoleucine, N-methylleucine, threonine, ornithine, serine, alanine, glycine, phenylalanine, cysteine, aspartic acid, glutamic acid and lysine.

X and Z are independently chosen from the group consisting of a covalent bond, an amino acid or a peptide. Each amino acid in X and Z is independently selected from the group of naturally occurring amino acids. X and Z are preferably covalent bonds.

$R^1$ is $R^3$—CO—.

$R^2$ is —$NR^4R^5$.

$R^3$ is selected from the group consisting of a lower alkyl group, a substituted lower alkyl group, an aryl group, a substituted aryl group, a heteroaryl group and a substituted heteroaryl group.

$R^4$ and $R^5$ are each independently selected from the group consisting of hydrogen, a lower alkyl group, a substituted lower alkyl group, an aryl group, a substituted aryl group, a heteroaryl group and a substituted heteroaryl group. $R^4$ and $R^5$ are not both —H. Taken together, $R^4$ and $R^5$ can also form a heterocyclic ring.

Taken together, X, Y and Z form a peptide containing no more than about fifteen amino acid residues.

The compound represented by Structural Formula (I) is a peptide having a group bonded to the nitrogen atom at the N-terminus and a second group bonded to the carbonyl at the C-terminus. In one aspect the peptide is linear. The N-terminus of Y is not bonded to arginine or an arginine derivative.

Optionally, the peptide formed by X, Y and Z is cyclized to form a ring. When cyclized, the ring can be formed by an amide linkage, an ester linkage or a disulfide linkage between two amino acids in the peptide. When the ring is formed by an amide linkage between the N-terminus and C-terminus of the peptide, $R^1$ and $R^2$ together form a covalent bond between the carbonyl at the C-terminus of the peptide and the nitrogen at the N-terminus of the peptide.

In another embodiment of the method of inhibiting the binding of a cell such as a leukocyte expressing a ligand for MAdCAM-1 on the cell surface (e.g., α4β7) to MAdCAM-1, for example endothelium expressing the molecule MAdCAM-1, the inhibitor administered is represented by Structural Formula (II):

$R^1$, $R^2$, X and Z are as defined for Structural Formula (I). Y' respresents a dipeptide having the sequence Asp-Thr, a tripeptide having the sequence Leu-Asp-Thr, or a pentapeptide $[AA]_1$-$[AA]_2$-$[AA]_3$-$[AA]_4$-$[AA]_5$ having the sequence Leu-Asp-Thr-Ser-Leu (SEQ ID NO: 1) with the proviso that any single one of $[AA]_1$, $[AA]_2$, $[AA]_3$, $[AA]_4$ or $[AA]_5$ can vary, being any naturally occurring amino acid. The nitrogen at the N-terminus of Y' may be bonded to any naturally occurring amino acid (including arginine) with the proviso that the N-terminus of Y' may not be bonded to glycine or sarcosine when Y' is Asp-Thr and the peptide formed from X—Y'-Z is cyclized, as described below.

X, Y' and Z taken together form a peptide containing no more than about fifteen amino acids. In one aspect the peptide formed by X, Y' and Z is linear. Preferably X and Z are each a covalent bond. Optionally, the peptide formed by X, Y' and Z is cyclized to form a ring. When cyclized, the ring can be formed by an amide linkage, an ester linkage or a disulfide linkage between two amino acids in the peptide. When the ring is formed by an amide linkage between the N-terminus and C-terminus of the peptide, $R^1$ and $R^2$ together form a covalent bond between the carbonyl at the C-terminus of the peptide and the nitrogen at the N-terminus of the peptide.

Another embodiment of the present invention is a novel compound. The compound is represented by Structural Formula II, as described above.

Another embodiment, of the present invention is a method of treating an individual suffering from a disease associated with leukocyte infiltration of tissues expressing the molecule MAdCAM-1. The method comprises administering to the individual a therapeutically effective amount of an inhibitor represented by Structure Formula (I) or an inhibitor represented by Structural Formula (II).

Compounds of the present invention are inhibitors of the binding of MAdCAM-1 to the receptor α4β7 and are therefore useful in the treatment of diseases such as inflammatory bowel disease with the potential for fewer side effects in other tissues where adhesion is mediated by α4β1 integrin, for example.

The compounds of the present invention are also useful in diagnostic and research applications. For example, the compounds can be used as immunogens (e.g., when conjugated to a suitable carrier) to induce the formation of antibodies which selectively bind MAdCAM-1 or a portion thereof. These antibodies can in turn be used to identify cells expressing MAdCAM-1 on their cell surface or detect MAdCAM-1 in a sample. In addition, the compounds of the present invention can be labelled and used to detect α4β7 integrin and/or quantitate expression on the surface of cells.

BRIEF DESCRIPTION OF THE DRAWINGS

FIG. 3 is a schematic illustration of a MAdCAM-1/mCκ fusion gene and encoded fusion protein. A BamHI site at the junction of the MAdCAM-1 and mCκ sequences introduces codons for Gly-Ser (SEQ ID NO: 63 and SEQ ID NO: 64). The fusion gene encodes the signal peptide (SEQ ID NO: 65 and SEQ ID NO: 66, partial signal peptide) and complete extracellular domain of MAdCAM-1 through the threonine residue at position 365. Single letter amino acid codes are used.

FIG. 4 is an illustration of the nucleotide sequence determined from subclones of cDNA clone 4 encoding human MAdCAM-1 (SEQ ID NO: 67), and the sequence of the predicted protein encoded by the open reading frame (MAdCAM-1) (SEQ ID NO: 68). The predicted signal peptide and transmembrane region are underlined in bold.

Figure 1:
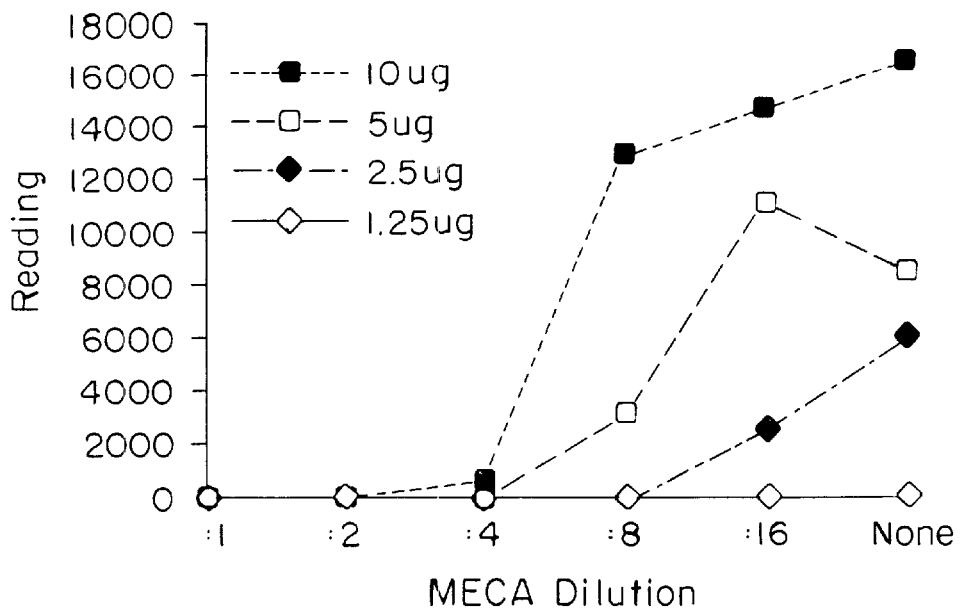
FIG. 1 is a graph illustrating a titration experiment used to select the amount of rat anti-murine κ capture antibody which was used in adhesion assays. MAdCAM-mCκ fusion protein was bound to the surface of a well via various amounts of capture antibody, and the adhesion of fluorescently labelled HUT 78 cells to fusion protein in the presence of increasing amounts of anti-MAdCAM-1 antibody was monitored. Reading (Y-axis) is in arbitrary flourescence units. 50 μl of a 10 μg/ml (■), 5 μg/ml (□), 2.5 μg/ml (♦) or 1.25 μg/ml (◇) solution of purified rat anti-murine κ antibody was used. Anti-murine MAdCAM-1 antibody MECA-367 was used as neat supernatant or diluted 1:2, 1:4, 1:8 or 1:16 (indicated on the X-axis by :1 (neat), :2, :4, :8, and :16, respectively). "None" indicates no MECA-367 antibody (buffer control) was present.

Cysteine residues of the two Ig-like domains are boxed, as are potential N-linked glycosylation sites. The mucin domain consisting of 71 amino acids is outlined by a thin bold line. The LDTSL (SEQ ID NO: 1) motif begins at amino acid 63.

FIG. 5 is an illustration of the nucleotide sequence determined from subclones of cDNA clone 20 encoding human MAdCAM-1 (SEQ ID NO: 69), and the sequence of the predicted protein encoded by the open reading frame (MAdCAM-1) (SEQ ID NO: 70). The predicted signal peptide and transmembrane region are underlined in bold. Cysteine residues of the two Ig-like domains are boxed, as are potential N-linked glycosylation sites. The mucin domain consisting of 47 amino acids is outlined by a thin bold line. The LDTSL (SEQ ID NO: 1) motif begins at amino acid 63. The two human cDNA clones are probably isoforms encoded by genomic DNA, generated, for example, by alternative splicing or by transcription of two different alleles.

DETAILED DESCRIPTION OF THE INVENTION

As used herein, "lower alkyl" refers to a hydrocarbon containing from one to about twelve carbon atoms. In one aspect the term "C3–C12 alkyl" is employed to include all lower alkyls except —CH$_3$ and —CH$_2$—CH$_3$. The hydrocarbon can be saturated or can contain one or more units of unsaturation. The hydrocarbon can also be branched, straight chained or cyclic.

A "cyclic hydrocarbon" refers to a cycloalkyl group. A "cycloalkyl group" includes carbocyclic rings (e.g., cyclopentyl and cyclohexyl) as well as carbocyclic rings in which one or more carbon atoms is replaced by a heteroatom (e.g., morpholino, piperidinyl, pyrollidinyl, thiomorpholino or piperazinyl). Also included are cycloalkyl rings fused to other cycloalkyl rings (e.g., decalinyl) or fused to aromatic or heteroaromatic groups (e.g., indanyl, tetralinyl and 9-xanthenyl). A "cyclic hydrocarbon" also includes bridged polycyclic structures such as adamantyl and nonbornyl. As with other lower alkyl groups, a cyclic hydrocarbon can be substituted.

As used herein, "aryl" groups are defined to include aromatic ring systems such as phenyl. "Heteroaryl" groups are defined to include aromatic ring systems which contain heteroatoms, such as 2-furanyl, 3-furanyl, 2-thienyl, 3-thienyl, 2-pyridyl, 2-pyranyl and 3-pyranyl. "Aryl" and "heteroaryl" groups also include fused polycyclic aromatic ring systems in which the aryl or heteroaryl ring is fused to one or more other aryl, heteroaryl or cycloalkyl rings. Examples include α-naphthyl, β-naphthyl, 1-anthracenyl, 2-anthracenyl, 2-benzothienyl, 3-benzothienyl, 2-benzofuranyl, 3-benzofuranyl, 2-indolyl, 2-quinolinyl, 3-quinolinyl, acridinyl and 9-thioxanthanyl. Also included are polycyclic aromatic ring systems in which aryl groups, heteroaryl groups or an aryl and a heteroaryl group are connected by a covalent bond (e.g., 4-phenylphenyl, 3,5-diphenylphenyl, 4-(2-thienyl)phenyl and 4-(2-furanyl) phenyl)) or a —(CH)$_n$— bridge (e.g., 4-(phenyl-CH$_2$) phenyl, 4-(phenylCH$_2$CH$_2$-)phenyl, 4-(—CH$_2$-2-thienyl) phenyl and 4-(—CH$_2$CH$_2$-2-thienyl)phenyl), wherein n is an integer from 1 to about 5.

Suitable substituents on a lower alkyl group, an aryl group or a heteroaryl group include C1–C2 alkoxy, ketone, aldehyde, (lower alkyl) ester, aryl, substituted aryl, heteroaryl, substituted heteroaryl benzyl, lower alkyl, fluoro, bromo, iodo, cyano, nitro and the like. A lower alkyl group, an aryl group or a heteroaryl group may have more than one substituent (e.g., 2,2,3,3-tetramethylcyclopropyl, 3,5-diphenylphenyl and 2,4-dichlorophenyl), 2-bromo-4-nitropentyl and 2-(3,5-dibromobenzofuranyl). In addition, a substituted lower alkyl group can have multiple substituents on one carbon atom (e.g., diphenylmethyl, triphenylmethyl, 2,2,3,3-tetramethylcyclopropyl and trifluoromethyl).

$R^1$ and $R^2$ are groups covalently bonded to the N-terminal and the C-terminal, respectively, of the peptide sequences of the compounds represented by Structural Formulas (I) and (II).

$R^3$ is preferably selected from the group consisting of adamantyl, adamantylmethyl, a C1–C4 alkyl group, a C3–C7 cycloalkyl group, a C3–C7 cycloalkyl group substituted with a C1–C4 alkyl group, an aryl group substituted with C3–C7 cycloalkyl group, phenyl substituted with a C1–C8 alkyl group, an aryl group, 2-anthracenyl, diphenylmethyl, 1-napthyl, 2-naphthyl, benzyl, indanyl, tetralinyl, triphenylmethyl, triphenyl(C1–C4 alkyl), 9-fluorenyl, styryl, a heteroaryl group, furanyl, thienyl, 9-xanthanyl, 9-thioxanthanyl, acridinyl, pyridyl, quinolinyl, a C1–C4 alkyl group substituted with an aryl group (e.g., benzyl and phenylethyl) and a C1–C4 alkyl group substituted with heteroaryl (furanylmethyl, thienylmethyl, pyridylmethyl, quinolinylmethyl). More preferably, $R^3$ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indolyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl.

$R^4$ and $R^5$ are preferably independently selected from the group consisting of a C1–C5 alkyl group, a C1–C5 alkyl group substituted with C1–C4 alkoxy, a C3–C7 cycloalkyl group, a C3–C7 cycloalkyl group substituted with a C1–C5 alkyl group, an aryl group, a substituted C1–C5 alkyl group (e.g., suitable substituents include a hydroxyl group, phenyl, substituted phenyl (e.g., suitable substituents include a C1–C5 alkyl group, C1–C4 alkoxy, halogen, nitro and trifluoromethyl)), a C1–C4 alkyl group substituted with an aryl group (e.g., benzyl, phenylethyl, diphenylethyl, 9-fluorenyl), a heteroaryl group (e.g., benzofuranyl, benzothienyl, furanyl, pyridinyl, quinolinyl, and thienyl) and a C1–C5 alkyl group substituted with a heteroaryl group (e.g., furanylmethyl, thienylmethyl, pyridylmethyl and quinolinylmethyl).

In addition, $R^4$ and $R^5$ may, taken together, form a heterocyclic ring including piperidinyl, pyrrolidinyl, morpholino, thiomorpholino or piperazinyl where the $N^4$-position of the piperazine ring is substituted by a group consisting of hydrogen, acetyl, benzoyl, alkyl, benzyl or phenyl. More preferably, $R^4$ and $R^5$ are each independently selected from the group consisting of 2-hydroxyethyl, benzyl, 2-benzofuranyl, 3-benzofuranyl, 2-benzothienyl, 3-benzothienyl, —$CH_2$-2-thienyl, —$CH_2$-3-thienyl, —$CH_2$-2-furanyl, —$CH_2$-3-furanyl, 3,4-dimethoxybenzyl, and isopentyl.

Examples of compounds of the present invention include the following:

Cpc-NH-Asp-Thr-N(CH2CH2OH)(Benzyl)

Cpc-NH-Asp-Thr-NH-Hexyl

Cpc-NH-Asp-Thr-NH-(3,4-Dimethoxy)(Benzyl)

Cpc-NH-Asp-Thr-NH—CH(Phenyl)$_2$

Idc-NH-Asp-Thr-NH-Benzyl

Chc-NH-Asp-Thr-NH—CH$_2$Thienyl

Bpc-NH-Asp-Thr-NH-Benzyl

Indc-NH-Asp-Thr-NH-Isopentyl

Bpc-NH-Asp-Thr-NH—CH$_2$Thienyl

Abbreviations are defined in Table 3.

In a preferred embodiment, $R^3$ is selected from the group consisting of diphenylmethyl, triphenylmethyl, trans 2-phenyl-ethylenyl, 2-phenyl-ethynyl, 2-benzofuranyl, 3-benzofuranyl, 2-benzothienyl and 3-benzothienyl, $R^4$ is selected from the group consisting of 2-hydroxyethyl, benzyl, 2-benzofuranyl, 3-benzofuranyl, 2-benzothienyl, 3-benzothienyl, —$CH_2$-2-thienyl, —$CH_2$-3-thienyl, —$CH_2$-2-furanyl, —$CH_2$-3-furanyl and $R^5$ is —H.

As used herein, "[AA]" represents an amino acid and "$[AA]_1 \ldots [AA]_n$" represents a peptide, wherein $[AA]_1$ is the N-terminal amino acid and $[AA]_n$ is the C-terminal amino acid. Unless otherwise indicated, amino acids in the peptides are presented from left to right, with the left end being the N-terminus and the right end being the C-terminus. The amino acids within the peptide can be similarly designated. For example, "$[AA]_2$" and "$[AA]_{n-1}$" refer to the second amino acid from the N-terminal and C-terminal, respectively. This nomenclature permits each amino acid of X and Z to be designated. For example, "$[AA]_1$ of Z" refers to the amino acid at the N-terminus of Z when Z is a peptide. "$[AA]_2$ of X" refers to the second amino acid from the N-terminus of X when X is a peptide. "$[AA]_{n-1}$ of X" refers to the second amino acid from the C-terminus of X when X is a peptide. It is to be understood that the amino acids in Y are numbered in sequence from 1–5 (Y' is numbered in sequence from 1–5, 1–3 or 1–2 when Y' is a pentapeptide, a tripeptide or a dipeptide, respectively) begining at the N-terminus and ending at the C-terminus. Thus, "$[AA]_2$ of Y" refers to the second amino acid from the N-terminal of Y. It is also to be understood that "$[AA]_1$ of X" (or "$[AA]_1$ of Z") can be used to represent X (or Z) when X (or Z) is a single amino acid.

In one embodiment Y is Y', e.g., Asp-Thr, Leu-Asp-Thr or a pentapeptide $[AA]_1$-$[AA]_2$-$[AA]_3$-$[AA]_4$-$[AA]_5$ having the sequence Leu-Asp-Thr-Ser-Leu (SEQ ID NO: 1) with the proviso that a single one of $[AA]_1$, $[AA]_2$, $[AA]_3$, $[AA]_4$ or $[AA]_5$ can vary, being any naturally occurring amino acid. A "naturally occurring amino acid" is an amino acid that occurs in nature. "Naturally occurring amino acids" includes, but are not limited to serine, threonine, cysteine, glycine, valine, alanine, leucine, isoleucine, aspartic acid, glutamic acid, glutamine, asparagine, lysine, arginine, ornithine, tyrosine, phenylalanine, histidine, proline, 4-hydroxyproline, tryptophan and methionine.

For Structural Formula (I), if X is an amino acid X may not be arginine or a derivative of arginine. In addition, for Structural Formula (I) if X is a peptide, the amino acid at the C-terminus of X may not be arginine or an arginine derivative. Arginine derivatives include N and/or N' C1–C4 alkylated arginines (e.g., N-alkyl arginine, N,N-dialkyl arginine, N,N'-dialkyl arginine, and N,N,N'-trialkyl arginine). Arginine derivatives also include arginine mimics (e.g., p-aminomethyl arginine), arginine isomers (e.g., norarginine), arginine having substituents in the side chain (e.g., nitro, halo or C1–C4 alkyl) and arginines containing one or more additional carbon atoms in the side chain (e.g., homoarginine).

In a preferred embodiment Y or Y' is the pentapeptide $[AA]_1$-$[AA]_2$-$[AA]_3$-$[AA]_4$-$[AA]_5$ wherein:

amino acid $[AA]_1$ is selected from the group consisting of leucine, isoleucine, alanine, valine, glycine, phenylalanine and N-methylleucine;

amino acid $[AA]_2$ is selected from the group consisting of aspartic acid, glutamic acid, phenylalanine and tyrosine;

amino acid $[AA]_3$ is selected from the group consisting of threonine, serine, valine, proline and 4-hydroxyproline;

amino acid $[AA]_4$ is selected from the group consisting of serine, cysteine and threonine; and amino acid $[AA]_5$ is selected from the group consisting of leucine, alanine, valine, isoleucine, alanine, glycine, phenylalanine and N-methylleucine.

In another aspect, any one or more of $[AA]_1$, $[AA]_2$, $[AA]_3$, $[AA]_4$ and $[AA]_5$ in the pentapeptide of Y or Y' can also be a non-naturally occurring amino acid. $[AA]_1$ and/or $[AA]_5$ can be a non-naturally occurring amino acid in which the side chain is a C2–C7 substituted or unsubstituted alkyl group or a substituted phenyl group. Side chain alkyl groups can be straight chained, branched or cyclic. Suitable substituents for an alkyl side chain include non-polar groups such as C1–C2 alkyl, halo, cyano, C1–C3 alkoxy, phenyl or substituted phenyl. Suitable substituents for a side chain phenyl group include non-polar groups such as C1–C2 alkyl, halo, cyano or —C1–C3 alkoxy. $[AA]_2$ can be a non-naturally occurring amino acid having a C3–C6 straight chained or branched alkyl group substituted with a carboxylic acid. $[AA]_3$ and/or $[AA]_4$ can be a non-naturally occurring amino acid in which the side chain is a C2–C6 straight chained or branched alkyl group substituted with an alcohol or thiol.

The compounds represented by Structural Formulas (I) and (II) are peptides X—Y-Z or X—Y'-Z, respectively, with groups attached to the N-terminus and C-terminus. Preferably, X and Z are covalent bonds, i.e. the compounds represented by Structural Formulas (I) and (II) are peptides Y or Y', respectively, with group $R^1$ attached to the N-terminal of Y or Y', and with group $R^2$ attached to the C-terminal of Y or Y'. In one aspect, X—Y-Z or X—Y'-Z is a linear peptide. In another aspect, X—Y-Z or X—Y'-Z is cyclized.

As used herein, "cyclized" refers to forming a ring by a covalent bond between suitable side chains of two amino acids in the peptide. For example, a disulfide can be formed between the sulfur atoms in the side chains of two cysteines. Alternatively, an ester can be formed between the carbonyl carbon in the side chain of, for example, glutamic acid or aspartic acid, and the oxygen atom in the side chain of, for example, serine or threonine. An amide can be formed between the carbonyl carbon in the side chain of, for example, glutamic acid or aspartic acid, and the amino nitrogen in side chain of, for example, lysine or ornithine.

"Cyclized" also refers to forming a ring by a peptide bond between the nitrogen atom at the N-terminus and the carbonyl carbon at the C-terminus. In this case, $R^1$ and $R^2$ together form a covalent bond.

"Cyclized" also refers to forming a ring by forming a covalent bond between the nitrogen at the N-terminus of the compound and the side chain of a suitable amino acid in the peptide. For example, an amide can be formed between the nitrogen atom at the N-terminus and the carbonyl carbon in the side chain of aspartic acid or glutamic acid. Alternatively, the compounds represented by Structural Formulas (I) and (II) can also be cyclized by forming a covalent bond between the carbonyl at the C-terminus of the compound and the side chain of a suitable amino acid in the peptide. For example, an amide can be formed between the carbonyl carbon at the C-terminus and the amino nitrogen atom in the side chain of lysine or ornithine; an ester can be formed between the carbonyl carbon at the C-terminus and the hydroxyl oxygen atom in the side chain of serine or threonine.

Preferably, the ring of the cyclized compounds of the present invention contains four to nine amino acids. The peptide is preferably cyclized to maximize within the ring the number of amino acids involved in the binding of the peptide to a ligand of MAdCAM-1, such as human α4β7. Thus, the ring contains at least four of the five amino acids in Y or Y', when Y or Y' is a pentapeptide. More preferably, the ring contains all of the amino acids in Y or Y'.

For compounds represented by Structural Formula (I), the ring can be formed by a bond between the side chain of an amino acid selected from the group consisting of $[AA]_{n-3}$ of X, $[AA]_{n-2}$ of X, $[AA]_{n-1}$ of X, $[AA]_n$ of X (if the specific amino acid is present in X) and $[AA]_1$ of Y and the side chain of any one of the amino acids selected from the group consisting of $[AA]_5$ of Y, $[AA]_1$ of Z, $[AA]_2$ of Z, $[AA]_3$ of Z and $[AA]_4$ of Z (if the specific amino acid is present in Z), with the proviso that the ring contains from four to nine amino acids. The ring can also be formed by a bond between the side chain of $[AA]_4$ and the side chains of $[AA]_{n-4}$ of X, $[AA]_{n-3}$ of X, $[AA]_{n-2}$ of X, $[AA]_{n-1}$ of X, $[AA]_n$ of X (if the specific amino acid is present in X) and $[AA]_1$ of Y when the ring contains only four of the five amino acids of Y.

For compounds represented by Structural Formula (II), when Y' is a pentapeptide the ring can be formed as described in the preceding paragraph. When Y' is a tripeptide, the ring can be formed by a bond between the side chain functional group of an amino acid selected from the group consisting of $[AA]_{n-5}$ of X, $[AA]_{n-4}$ of X, $[AA]_{n-3}$ of X, $[AA]_{n-2}$ of X, $[AA]_{n-1}$ of X, $[AA]_n$ of X and $[AA]_1$ of Y' and the side chain functional group of any one of the amino acids selected from the group consisting of $[AA]_3$ of Y', $[AA]_1$ of Z, $[AA]_2$ of Z, $[AA]_3$ of Z, $[AA]_4$ of Z, $[AA]_5$ of Z and $[AA]_6$ of Z (if the specific amino acid is present in X and/or Z), with the proviso that the ring contains from four to nine amino acids. When Y' is a dipeptide, the ring can be formed by a bond between the side chain of an amino acid selected from the group consisting of $[AA]_{n-6}$ of X, $[AA]_{n-5}$ of X, $[AA]_{n-4}$ of X, $[AA]_{n-3}$ of X, $[AA]_{n-2}$ of X, $[AA]_{n-1}$ of X, $[AA]_n$ of X and $[AA]_1$ of Y' and the side chain functional group of any one of the amino acids selected from the group consisting of $[AA]_3$ of Y', $[AA]_1$ of Z, $[AA]_2$ of Z, $[AA]_3$ of Z, $[AA]_4$ of Z, $[AA]_5$ of Z, $[AA]_6$ of Z and $[AA]_7$ of Z (if the specific amino acid is present in X and/or Z), with the proviso that the ring contains from four to nine amino acids.

When the ring contains all of the amino acids of Y or Y', the compound of Structural Formula I or II can be cyclized by a peptide bond between the nitrogen at the N-terminus of X and the carbonyl carbon at the C-terminal of Z.

In one embodiment, X is an amino acid or has an amino acid sequence which is the same as that immediately N-terminal to the LDTSL motif of human MAdCAM-1, and Z is an amino acid or has an amino acid sequence which is the same as that immediately C-terminal to the LDTSL (SEQ ID NO: 1) motif of human MAdCAM-1. In a further aspect, any one or two amino acids in X and Z can replaced by a naturally occurring amino acid or a non-naturally occurring amino acid, as described above.

Peptide sequences in the compounds of the present invention may be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides,* C. H. Li, Ed., Academic Press, 1983, pp. 48–267; and Barany and Merrifield, in *The Peptides,* E. Gross and J. Meienhofer, Eds., Academic Press, New York, 1980, pp. 3–285. Methods of solid phase peptide synthesis are described in Merrifield, R. B., *Science,* 232: 341 (1986); Carpino, L. A. and Han, G. Y., *J. Org. Chem.,* 37: 3404 (1972); and Gauspohl, H. et al., *Synthesis,* 5: 315 (1992)). The teachings of these six articles are incorporated herein by reference in their entirety. Examples of the synthesis of the compounds having the structure represented by Structural Formulas (I) and (II) are disclosed in Examples 1, General Procedures A–C.

Methods of cyclizing compounds having peptide sequences are described, for example, in Lobl et al., WO 92/00995, the teachings of which are incorporated herein by reference in their entirety. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protection such as allyl (OAI) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd° and Acm is easily removed by iodine treatment. Examples of cyclizing a compound represented by Structural Formulas (I) and (II) by forming a disulfide bond are given in Example 1 and General Procedure D.

Methods

Peptides which mimic the conserved amino acid motif LDTSL (SEQ ID NO: 1) and which are modified at the N- and C-termini, including the compounds of the present invention, are useful in a method of inhibiting (e.g., reducing or preventing) the binding of a cell bearing a ligand of MAdCAM-1 on the cell surface to MAdCAM-1 or a portion thereof (e.g., the extracellular domain). According to the method, the cell bearing a ligand for MAdCAM-1 is contacted with an effective amount of an (i.e., one or more) inhibitor. As used herein, an inhibitor is a compound which inhibits (reduces or prevents) the binding of MAdCAM-1 to a ligand, including $\alpha 4\beta 7$ integrin, and/or which inhibits the triggering of a cellular response mediated by the ligand. An effective amount can be an inhibitory amount (such as an amount sufficient to achieve inhibition of adhesion of a cell bearing a MAdCAM-1 ligand to MAdCAM-1). Ligands for MAdCAM-1 include $\alpha 4\beta 7$ integrins, such as human $\alpha 4\beta 7$ integrin, and its homologs from other species such as mice (also referred to as $\alpha 4\beta p$ or LPAM-1 in mice).

For example, the adhesion of a cell which naturally expresses a ligand for MAdCAM-1, such as a leukocyte (e.g., B lymphocyte, T lymphocyte) or other cell which expresses a ligand for MAdCAM-1 (e.g., a recombinant cell), to MAdCAM-1 can be inhibited in vivo or in vitro according to the method. In one embodiment, the MAdCAM-mediated interaction of a first cell bearing a ligand for MAdCAM-1 with a second cell bearing MAdCAM-1 is inhibited by contacting the first cell with an inhibitor according to the method.

The adhesion of cells to MAdCAM-1 or a suitable portion thereof can be inhibited. For example, MAdCAM-1 or a suitable portion thereof can be a soluble protein or can be expressed on the surface of a suitable cell, such as a cell which naturally expresses MAdCAM-1 (e.g., an endothelial cell), a suitable cell line, or other cell which expresses MAdCAM-1 (e.g., a recombinant cell). Suitable portions of MAdCAM-1 include, for example, a portion comprising the LDTSL (SEQ ID NO: 1) motif capable of mediating adhesion (e.g., a portion comprising the entire extracellular domain, or both N-terminal immunoglobulin-like domains). MAdCAM-1 or a portion thereof can be part of a larger molecule, such as a fusion protein. For example, a soluble hybrid protein comprising a mammalian (e.g., human or other primate, murine) MAdCAM-1 moiety fused at its C-terminus, to the N-terminus of an immunoglobulin moiety (e.g., one or more immunoglobulin constant regions) to obtain an immunoadhesin, such as those prepared according to Capon et al. (U.S. Pat. No. 5,428,130), can be used. For example, as shown herein, the adhesion of a T cell lymphoma line which expresses $\alpha 4\beta 7$ to a fusion protein comprising the extracellular domain of murine MAdCAM-1 joined to the constant region of a murine κ light chain was inhibited according to the method (See e.g., Example 2 and Table 2). These or other recombinant soluble receptor molecules are useful in the method.

In another aspect, the invention relates to a method of treating an individual (e.g., a mammal, such as a human or other primate) suffering from a disease associated with leukocyte (e.g., lymphocyte, monocyte) infiltration of tissues (including recruitment and/or accumulation of leukocytes in tissues) which express the molecule MAdCAM-1. The method comprises administering to the individual a therapeutically effective amount of an inhibitor (i.e., one or more inhibitors) of Structural Formula (I) or Structural Formula (II). For example, inflammatory diseases, including diseases which are associated with leukocyte infiltration of the gastrointestinal tract (including gut-associated endothelium), other mucosal tissues, or tissues expressing the molecule MAdCAM-1 (e.g., gut-associated tissues, such as venules of the lamina propria of the small and large intestine; and mammary gland (e.g., lactating mammary gland)), can be treated according to the present method. Similarly, an individual suffering from a disease associated with leukocyte infiltration of tissues as a result of binding of leukocytes to cells (e.g., endothelial cells) expressing the molecule MAdCAM-1 can be treated according to the present invention.

Diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis.

Pancreatitis and insulin-dependent diabetes mellitus are other diseases which can be treated using the present method. It has been reported that MAdCAM-1 is expressed by some vessels in the exocrine pancreas from NOD (nonobese diabetic) mice, as well as from BALB/c and SJL mice. Expression of MAdCAM-1 was reportedly induced on endothelium in inflamed islets of the pancreas of the NOD mouse, and MAdCAM-1 was the predominant addressin expressed by NOD islet endothelium at early stages of insulitis (Hanninen, A., et al., *J. Clin. Invest.*, 92: 2509–2515 (1993)). Further, accumulation of lymphocytes expressing $\alpha 4\beta 7$ within islets was observed, and MAdCAM-1 was implicated in the binding of lymphoma cells via $\alpha 4\beta 7$ to vessels from inflamed islets (Hanninen, A., et al., *J. Clin. Invest.*, 92: 2509–2515 (1993)).

Examples of inflammatory diseases associated with mucosal tissues which can be treated according to the present method include mastitis (mammary gland), cholecystitis, cholangitis or pericholangitis (bile duct and surrounding tissue of the liver), chronic bronchitis, chronic sinusitis, asthma, and graft versus host disease (e.g., in the gastrointestinal tract). As seen in Crohn's disease, inflammation often extends beyond the mucosal surface, accordingly chronic inflammatory diseases of the lung which result in interstitial fibrosis, such as hypersensitivity pneumonitis, collagen diseases, sarcoidosis, and other idiopathic conditions can be amenable to treatment.

Some studies have suggested that the cell adhesion molecule, ICAM-1, can mediate leukocyte recruitment to inflammatory sites through adhesion to leukocyte surface ligands, i.e., Mac-1, LFA-1 or $\alpha 4\beta 1$ (Springer, *Nature*, 346:425–434 (1990)). In addition, vascular cell adhesion molecule-1 (VCAM-1), which recognizes the $\alpha 4\beta 1$ integrin (VLA-4), has been reported to play a role in in vivo leukocyte recruitment (Silber et al., *J. Clin. Invest.* 93:1554–1563 (1994)). It has been proposed that IBD can be treated by blocking the interaction of ICAM-1 with LFA-1 or Mac-1, or of VCAM-1 with $\alpha 4\beta 1$ (e.g., WO 93/15764). However, these therapeutic targets are likely to be involved in inflammatory processes in multiple organs, and a functional blockade could cause systemic immune dysfunction.

In contrast to VCAM-1 and ICAM-1, MAdCAM-1 is preferentially expressed in the gastrointestinal tract and mucosal tissues, binds the α4β7 integrin found on lymphocytes, and participates in the homing of these cells to mucosal sites, such as Peyer's patches in the intestinal wall (Hamann et al., J. Immunol., 152:3282–3293 (1994)). As inhibitors of the binding of MAdCAM-1 to α4β7 integrin, the compounds of the present invention have the potential for fewer side effects due to e.g., effects on other tissue types where adhesion is mediated by other receptors, such as α4β1 integrin.

According to the method, an inhibitor can be administered to an individual (e.g., a human) alone or in conjunction with another agent, such as an additional pharmacologically active agent (e.g., sulfasalazine, an antiinflammatory compound, or a steroidal or other non-steroidal antiinflammatory compound). A compound can be administered before, along with or subsequent to administration of the additional agent, in amounts sufficient to reduce or prevent MAdCAM-mediated binding to a ligand for MAdCAM-1, such as human α4β7.

An effective amount of an inhibitor can be administered by an appropriate route in a single dose or multiple doses. An effective amount is a therapeutically effective amount sufficient to achieve the desired therapeutic and/or prophylactic effect (such as an amount sufficient to reduce or prevent MAdCAM-mediated binding to a MAdCAM ligand, thereby inhibiting leukocyte adhesion and infiltration and associated cellular responses. Suitable dosages can be determined by methods known in the art and can be dependent, for example, upon the individual's age, sensitivity, tolerance and overall well-being. For example, dosages can be from about 0.1 mg/kg to about 50 mg/kg body weight per treatment.

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Oral and parenteral administration are preferred modes of administration.

Formulation of an inhibitor to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. (1980)). For inhalation, the compound can be solubilized and loaded into a suitable dispenser for administration (e.g., an atomizer, nebulizer or pressurized aerosol dispenser).

The present method can be used to assess the inhibitory effect of a compound of the present invention and of other potential antagonists useful in the method on the interaction of MAdCAM-1 with a ligand for MAdCAM-1 in vitro or in vivo. For example, compounds of the present invention were assayed for their ability to inhibit MAdCAM-1 binding to human α4β7 integrin using an adhesion assay described in Example 2. Other suitable assays can be used to assess the ability of compounds to inhibit binding of MAdCAM-1 to a ligand for MAdCAM-1. For example, other fusion proteins (e.g., a chimeric protein or "immunoadhesin") can be constructed and used in an assay such as the assay described in Example 2 or other suitable assays. A fusion protein comprising human MAdCAM-1 or a portion thereof (e.g., the entire extracellular domain or the two N-terminal immunoglobulin domains) joined to an immunoglobulin heavy or light chain constant region can be produced and used in an assay similar to that described in Example 2, using a capture antibody suitable for the immunoglobulin constant region selected. In a different assay, unlabeled cells bearing a MAdCAM-1 ligand can be contacted with such a fusion protein under conditions suitable for binding to the ligand in the presence or absence of compound, and the amount of bound chimeric protein determined (e.g., cells can be removed and the amount of chimeric protein bound determined by, flow cytometry or other suitable methods).

Compounds suitable for use in therapy can also be evaluated in vivo, using suitable animal models. Suitable animal models of inflammation have been described. For example, NOD mice provide an animal model of insulin-dependent diabetes mellitus. CD45 RB$^{Hi}$/SCID model provides a model in mice with similarity to both Crohn's disease and ulcerative colitis (Powrie, F. et al., *Immunity*, 1: 553–562 (1994)). Captive cotton-top tamarins, a New World non-hman primate species, develop sponataneous, often chronic, colitis that clinically and histolgocially resembles ulcerative colitis in humans (Madara, J. L. et al., *Gastroenterology*, 88: 13–19 (1985)). The tamarin model and other animal models of gastrointestinal inflammation using BALB/c mice (a (DSS)-induced inflammation model; DSS, dextran sodium sulfate) and common marmosets are described in Briskin et al., U.S. Ser. No. 08/523,004, filed Sep. 1, 1995, the teachings of which are incorporated herein by reference in their entirety. Knockout mice which develop intestinal lesions similar to those of human inflammatory bowel disease have also been described (Strober, W. and Ehrhardt, R. O., *Cell*, 75: 203–205 (1993)).

Preferably, selective inhibition of the interaction of MAdCAM-1 with a ligand thereof is achieved. Selective inhibition can be assessed, for example, by further evaluating the effect of compounds on adhesion between one or more other receptor-ligand pairs. For example, adhesion assays which assess the interaction of a particular receptor and ligand pair, such as (a) VCAM-1 and α4β1, (b) ICAM-1 and LFA-1, (c) fibronectin and α5β1, and (d) fibronectin and α4β1, can be conducted. Nonlimiting examples of suitable cell lines for such adhesion assays include (a) RAMOS cells, (b) JY cells, (c) K562 cells, and (d) RAMOS cells, respectively. In these assays, isolated and/or recombinant fibronectin (Sigma Chemical Co., St. Louis, Mo.), VCAM-1, ICAM-1, or fusion proteins comprising the ligand binding domain (s) of VCAM-1 or ICAM-1, can be used, for example.

The compounds of the present invention can also be used as immunogens to produce antibodies, including monoclonal and polyclonal antibodies, against MAdCAM-1 using methods known in the art or other suitable methods (see e.g., Kohler et al., *Nature*, 256:495–497 (1975); Galfre, G., et al., *Nature*, 299:550–552 (1977); Harlow et al., 1988, Antibodies: A Laboratory Manual, (Cold Spring Harbor, N.Y.); or Current Protocols in Molecular Biology, Vol. 2 (Supplement 27, Summer '94), Ausubel et al., Eds. (John Wiley & Sons: New York, N.Y.), Chapter 11 (1991)). Antibodies can be raised against an appropriate immunogen in a suitable mammal (e.g., a mouse, rat, rabbit or sheep). For example, a compound represented by Structural Formulas (I) and (II)

or a variant thereof can be produced and used as an immunogen to raise antibodies in a suitable immunization protocol.

Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA).

Antibodies and monoclonal antibodies produced as described have a variety of uses. For example, those against or reactive with MAdCAM-1, and preferably which bind specifically to MAdCAM-1, can be used to identify and/or sort cells exhibiting MAdCAM-1 on the cell surface (e.g., in flourescence activated cell sorting, histological analyses). Monoclonal antibodies specific for MAdCAM-1 can also be used to detect and/or quantitate MAdCAM-1 expressed on the surface of a cell or present in a sample (e.g., in an ELISA). Antibodies reactive with the immunogen are also useful. For example, they can be used to detect and/or quantitate immunogen in a sample, or to purify immunogen (e.g., by immunoaffinity purification).

This invention further relates to the diagnostic use or research of antagonists of MAdCAM in the detection and/or quantitation of $\alpha 4\beta 7$ integrin present on leukocytes using a suitable label or indicator. For example, hydrocarbon fluorescence indicators such as a pyrene moiety, or radioisotope labels such as $^{125}I$ can be attached to the aryl ring of the N-terminus functional group of the antagonist peptide of this invention. The fluorescence properties of pyrene ring derivatives have been reported (I. A. Prokhorenko, et al., *Bioorg. Med. Chem. Lett.*, 5:2081 (1995)). The use of labeled peptides for identifying cells having a membrane-bound protein is described in Riper et al., *J. Exp. Med.* 177:851 (1993).

This diagnostic tool would be valuable in the identification of $\alpha 4\beta 7$-positive leukocytes from subjects with suspected inflammatory bowel diseases and the like. Antagonist molecules of this invention possessing this indicator grouping are described as examples of the invention with adhesion antagonist properties.

EXEMPLIFICATION

The present invention will now be illustrated by the following Examples, which are not intended to be limiting in any way.

EXAMPLE 1

Synthesis

The novel compounds of this invention can be synthesized according to the general procedures of synthesis, A–D, utilizing solid-phase peptide synthesis methodology described herein, which are known to person skilled in the art, or other suitable techniques. See e.g., Merrifield, R. B., *Science*, 232: 341 (1986); Carpino, L. A., Han, G. Y., *J. Org. Chem.*, 37: 3404 (1972); Gauspohl, H., et al., *Synthesis*, 5: 315 (1992)).

For multiple peptide synthesis the Fmoc/t-Bu protocol was used. In situ activation of the amino acid derivative was performed by benzotriazolyl-N-oxytripyrrolidinophosphoniumhexaflurophosphate (PYBOP) or 2(1-benzotriazolyl-1-yl)-1,1,3,3-tetramethyluronium (HBTU) and N-methylmorpholine (NMM) in dimethylformamide (DMF) as a solvent. In order to improve the coupling efficiency and quality of the final peptides, each coupling reaction was carried out twice. As a solid support Rink Amide Am Resin (4-[2'-4-dimethoxyphenyl-Fmoc-aminomethyl]-phenoxyacetamido-norleucylaminoethyl resin) was used due to its high loading and excellent swelling properties. Fmoc group was removed by 10% piperidine and 2% DBU in DMF. The peptides were cleaved from the resin and the side chain protecting groups were simultaneously removed by a trifluoroacetic acid (TFA) cocktail. All peptides reported in Table 2 below are carboxy-terminus blocked as the carboxamide. More details of the peptide synthesis protocol are given below.

HPLC and mass spectral analysis

All of the crude peptides were analyzed by reversed phase HPLC using DELTAPAK C18, 5 $\mu$m column, eluted with a linear gradient of 0.1% TFA in $CH_3CN$/water (100% $CH_3CN$/0% water) to 0.1% TFA in $CH_3CN$/water (0% $CH_3CN$/100% water) over a 30 minute period with flow rate of 1 ml/minute. The purity of the samples were determined and were essentially found to contain one component. This was confirmed by matrix-assisted laser desorption ionization time of flight mass spectral analysis (MALDI-TOF, Kratos, Inc.) internally referenced to leucine-enkephalin and sinapinic acid. Generally, the peptides gave the mass within 1%, of MH+ or M+Na+ or within experimental error of the calculated value.

General Procedure A, Peptide Synthesis

These peptides were synthesized via Fmoc/t-Butyl chemistry on a Gilson 421 automated multiple peptide synthesizer starting with Fmoc-Am-PS (100 mg, 0.5 mmol/g) resin. Acylations were carried out twice with the Fmoc-amino acid (5 equivalents), HBTU (5 equivalents)/NMM (10 equivalents) using 20–45 minute coupling time. Fmoc deprotection was carried out with 20% piperidine in DMF for 24 minutes. Treatment with Reagent-R (TFA-EDT-thioanisole-anisole, 90:5:3:2) for 2 hours was used to deblock and remove the peptides from the resin. The peptides were then precipitated from ether and lyophilized from acetic acid.

General Procedure B, Peptide Synthesis

Peptides were synthesized via Fmoc/t-Butyl chemistry on a Gilson 421 automated multiple peptide synthesizer starting with Fmoc-Am-PS (50 mg, 0.5 mmol/g) resin. Acylations were carried out twice with the Fmoc-amino acid (10 equivalents), HBTU (10 equivalents)/NMM (20 equivalents) or PYBOP (10 equivalents)/NMM (20 equivalents) using a 20–45 minute coupling time. Fmoc deprotection was carried out with 2% 1,8-diazobicyclo[5,4.0]undec-7-ene (DBU) and 10% piperidine in DMF for 24 minutes. Treatment with Reagent-R (TFA-EDT-thioanisole-anisole, 90:5:3:2) for 2 hours was used to deblock and remove the peptides from the resin. The peptides were then precipitated from ether and lyophilized from acetic acid.

General Procedure C, Synthesis of N-Acylated Peptides

The peptides were synthesized via Fmoc/t-Butyl chemistry on a Gilson 421 automated multiple peptide synthesizer starting with Fmoc-Am-PS (50 mg, 0.5 mmol/g) resin. Acylations were carried out twice with the Fmoc-amino acid (10 equivalents), HBTU (10 equivalents)/NMM (20 equivalents) or PYBOP (10 equivalents)/NMM (20 equivalents) using 20–45 minute coupling time. For the final acylation the Fmoc-amino acid was substituted with an appropriate organic acid. Fmoc deprotection was carried out with 2% DBU and 10% piperidine in DMF for 24 minutes. Treatment with Reagent-R (TPA-EDT-thioanisole-anisole, 90:5:3:2) for 2 hours was used to deblock and remove the peptides from the resin. The peptides were then precipitated from ether and lyophilized from acetic acid.

General Procedure D, Synthesis Peptides Cyclized Through A Disulfide Bond

The linear acyclic peptides were synthesized as described above in the General Procedure B. The acetamidomethyl (Acm) protecting group from the cysteine side chain was simultaneously removed and peptides were cyclized by iodine treatment. A solution of 25 mg of iodine in 5 mL of 80% aqueous acetic acid was added to 5 mg of peptide. The mixture was shaken at room temperature for 2 hours, diluted with water (25 ml), extracted with chloroform (3×25 ml) and finally lyophilized to give the cyclized peptide.

Syntheses of K*LDTSLD* (SEQ ID NO: 2) Cyclized Between the Side Chains of Lysine and the N-Terminal Aspartic Acid The K*LDTSLD* ("*" indicates a cyclizing amino acid) peptide is assembled on PAL-PEG-PS-resin using Nα-Fmoc-amino acids and t-butyl side-chain protection as described in General Procedures A and B, except D* and K* are incorporated in the linear chain as Fmoc-Asp(OAl)-OH and Fmoc-Lys(Aloc)-OH, respectively. Allyl functions are removed by treatment with $Pd(PPH_3)_4$, morpholine and triphenylphosphine in dry THF at room temperature and cyclization is achieved with PYBOP. Finally the peptide is deblocked and removed from the resin as described in General Procedures A and B.

Synthesis of Head to Tail Cyclic Peptides

The TSLLD peptide SEQ ID NO: 62 is assembled on Fmoc-Asp(OPAC-resin)-OAl using Fmoc-amino acids and t-butyl side-chain protection, as described in General Procedures A and B. The allyl function is removed by treatment with $Pd(PPh_3)_4$, morpholine and triphenylphosphine in dry THF at room temperature and cyclization is achieved with PYBOP. Finally the peptide is deblocked and removed from the resin as described in General Procedures A and B to give cyclic LDTSL peptide (SEQ ID NO: 62). Kates, S. A., et al., "Peptides: Design, Synthesis and Biological Activity," Basava C, Anantharamalah G M, eds., pp. 39–58 Boston: Birkhauser.

EXAMPLE 2

Biological Activity

The compounds of the present invention were evaluated for their biological properties. Table 2 lists a number of compounds of the present invention, their physical characterization, and their ability to inhibit the adhesion of α4β7-bearing cells (HUT 78 cells) to MAdCAM-1 (described as percent inhibition at the concentration noted or by the corresponding $IC_{50}$ value ($\mu$m) determined using the adhesion assay described below. $IC_{50}$ corresponds to the concentration of compound which inhibits 50% of the total number of cells adhering to MAdCAM-1 in a control conducted in the absence of inhibitor.

Overview

A soluble fusion protein comprising murine MAdCAM-1 was produced in a baculovirus expression system and used in the adhesion assay. A fusion gene in which sequences encoding the signal peptide and extracellular domain of murine MAdCAM-1 were fused to sequences encoding a constant region of the murine kappa light chain ($mC_\kappa$) was constructed, and cloned into a baculovirus shuttle vector. Fusion protein produced from the resulting construct contained the integrin binding sequences of murine MAdCAM-1 at the amino-terminus, and the mCκ sequence at the carboxy-terminus. Recombinant baculovirus encoding the fusion protein was harvested from infected Sf9 insect cells. Fusion protein was detected in supernatants of infected Sf9 cells by ELISA assay, using a horseradish peroxidase-linked polyclonal anti-mCκ antibody and chromogenic substrate according to standard protocols. Recombinant protein was also verified by immunoprecipitation with anti-murine MAdCAM-1 monoclonal antibody (MAb MECA-367).

For adhesion assays, a dose response curve obtained using increasing amounts of rat anti-mCκ MAb indicated the amount of rat anti-mCκ MAb to be used as capture antibody in the assay. Subsequently, an IC50 for Ac-LDTSL-NH2 was determined to be 278 $\mu$M.

Human T-cell lymphoma cells (HUT 78 cells) activated with $Mn^{+2}$ were used for the adhesion assay in a 96-well format. HUT 78 cells were labelled by preincubation with BCECF-AM stain (Molecular Probes). Assays were conducted in a final volume of 200 $\mu$l. The adhesion of HUT 78 cells to MAdCAM-1/mCκ fusion protein bound to wells via rat anti-mCκ capture antibody was assessed in the presence or absence of each compound. Adhesion of HUT 78 cells was monitored using a fluorescent plate reader at a setting gain of 10 at 485/535 nM. Percent inhibition and $IC_{50}$ values were determined.

Production of MAdCAM-1/mCκ Fusion Protein Antibodies, Cells and Viruses

Affinity-purified polyclonal goat-anti-mouse-C-kappa ($mC_\kappa$) antibodies (#M33100), horseradish peroxidase-linked goat anti-$mC_\kappa$ antibodies (#M33107), and alkaline phosphatase-linked swine anti-goat H & L chains (#G50008) were purchased from Caltag. Sepharose-linked rat anti-$mC_\kappa$ affinity matrix was obtained from Zymed.

Affinity purified rat-anti-$mC_\kappa$ monoclonal antibodies were prepared by Dr. Hans Peter Kocher (BTC) from the rat hybridoma cell line 187.1 (American Type Culture Collection, 12301 Parklawn Drive, Rockville, Md. 20852, Accession No. ATCC HB 58), and were linked to cyanogen bromide-activated Sepharose 4B for affinity purification of proteins.

ACMNPV DNA and cationic liposomes (Invitrogen transfection kit #B825-03) or lipofectin (GIBCO/BRL #82925A) were used to transfect Sf9 insect cells (American Type Culture Collection, Accession No. ATCC CRL 1711; gift from Dr. Max Summers) in HyQ serum-free medium (Hyclone, #B-5502-L-P). BaculoGold (Pharmingen) was also used in some transfections. Cells were maintained in TNM-FH medium (GIBCO BRL) supplemented with 10 fetal bovine serum and 0.1% F-68 pluronic acid (GIBCO/BRL, #670-404AG).

Construction of pVL941/$mC_\kappa$

Based on the published sequence for the mouse kappa constant region ($mC_\kappa$; Hieter, P. A., et al., *Cell* 22: 197–207 (1980)), two oligonucleotides having the following sequences (SEQ ID NO: 3 and SEQ ID NO: 4, respectively) were designed and synthesized:

5' primer

5'-GGATCC GCT GAT GCT GCA CCA ACT GTA TTC-3'

3' primer

5'-CCT TTG TCC TAA CAC TCA TTC CTG TT-3'

The $mC_\kappa$ coding sequence was amplified by polymerase chain reaction (PCR) from the plasmid pVL91A3 containing the full-length 91A3 mouse kappa light chain (Meek, K., et al., *Proc. Natl. Acad. Sci. U.S.A.*, 84: 6244–6248 (1987)). An in-frame BamHI restriction site (underlined in the sequence above) was incorporated at the 5'-end of the coding sequence to facilitate fusion with MAdCAM-1 sequences.

Vector pVL941 (Invitrogen) was linearized by digestion at the unique BamHI site in the polyhedrin gene, and the ends were made blunt with the Klenow fragment of DNA polymerase. The amplified DNA fragment (312 base pairs) containing the 91A3 mouse kappa light chain was then ligated to pVL941 to yield pVL941/mC$_\kappa$. Clones containing the mC$_\kappa$ sequence in the same 5' to 3' orientation as the polyhedrin promoter were selected.

Construction of Baculovirus Shuttle Vector

Based on the published nucleotide sequence of murine MAdCAM-1 (Briskin, M. J. et al., Nature, 363: 461–464 (1993)), oligonucleotide primers having the following sequences (SEQ ID NO: 5 and SEQ ID NO: 6, respectively) were designed and synthesized:

5' primer

5'-GAT CAG GGA TCC ATG GAA TCC ATC CTG GCC CTC CTG-3'

3' primer

5'-TCG ATC GGA TCC GGT GGA GGA GGA ATT CGG GGT CA-3'

The ATG start codon of MAdCAM-1 is indicated in bold. The 5' and 3' primers each incorporated a BamHI restriction site for cloning into the expression vector (underlined above). Murine MAdCAM-1 sequences were amplified by PCR using these 5'- and 3'-primers. The product was digested with BamHI and inserted into vector pVL941/mC$\kappa$, which had been digested with BamHI. DNA fragments cloned into the BamHI site were screened for the correct orientation with respect to the mC$\kappa$ sequence. Fusion proteins produced from the resulting construct contained mouse MAdCAM-1 sequences at the N-terminus, and the mC$_\kappa$ sequence at the carboxy-terminus (FIG. 3). A two-amino acid glycine-serine spacer encoded by the six nucleotides corresponding to the BamHI restriction site forms the junction between these sequences.

Transfection of Sf9 Insect Cells

Co-transfection (lipofection) of Sf9 insect cells with a mixture of 1 $\mu$g of ACMNPV DNA (Invitrogen), 3–5 $\mu$g of shuttle vector DNA (pVL941/MAdCAM-1/mC$\kappa$ purified by magic-mini prep, Promega) and cationic liposomes (30 $\mu$l) was performed according to the manufacterers' instructions, with slight modifications. 2×10$^6$ cells in TNM-FH medium (10% FBS) were plated out in 60 mm dishes and allowed to attach over a 2–4 hour period prior to transfection. The medium was removed and the adherent cells were washed twice with serum-free medium (HyQ). Three ml of HyQ containing the DNA/liposome mixture were applied dropwise over the cells; the cells were incubated overnight. The medium was then removed by aspiration and 5 ml TNF-FN medium containing 10% FBS was added to each dish. After 48 hours, one ml was removed for plaque purification of recombinant virus, as previously described (O'Reilly, D. R., et al., (Eds.), Baculovirus Expression Vectors (W. H. Freeman and Co.: New York), pp. 124–128 (1992)).

ELISA Assay of Transfected Sf9 Cells

For each transfection, triplicate wells were coated with polyclonal goat anti-mC$_\kappa$ antibodies (2 $\mu$g/ml in carbonate/bicarbonate buffer), and incubated overnight. The plates were washed three times with phoshate buffered saline (PBS) containing 0.5% Triton X-100, and 0.5 M NaCl and then washed twice with PBS. This washing protocol was used between all steps. The wells were then blocked with 2% BSA in TBS for one hour. Supernatant (100 $\mu$l) taken from cells four to five days post-infection was applied to each well and incubated at 37° C. for 2 hours. The presence of mC$_\kappa$ fusion protein was detected by the addition of horseradish peroxidase-linked polyclonal anti-mC$_\kappa$ antibody and chromogenic substrate, according to standard protocols.

Imunodetection of mC$_\kappa$ fusion proteins

Recombinant virus containing the MAdCAM-1/mC$\kappa$ fusion gene was isolated by plaque purification, and amplified by infecting Sf9 insect cells (2×10$^6$ cells/60 mm petri dish) in 5 ml TNM-FH medium. From this 5 ml stock, an aliquot (100 $\mu$l) was taken to infect 2×10$^6$ Sf9 cells as before. Supernatants (10 $\mu$l) taken 24, 48, 72 and 96 hours post-infection were assayed for the presence, accumulation and stability of mC$_\kappa$ fusion protein by Western blot analysis. Samples were applied to 10% SDS/PAGE gels. Proteins were electrophoretically transferred to nitrocellulose by standard techniques. The fusion protein was detected by addition of polyclonal goat anti-mC$_\kappa$ antibodies (2 $\mu$g) in 5 ml BLOTTO (5%) followed by treatment with alkaline phosphatase-linked swine anti-goat H & L chains and chromogenic substrate (BIORAD, Catalog No. 170-6432).

Purification of mC$_\kappa$ fusion protein by affinity chromatography

Production of fusion proteins was carried out in stirred microcarrier flasks. Sf9 insect cells (2×10$^6$ cells/ml) were infected with virus particles containing the MAdCAM-1/mC$\kappa$ fusion gene at a multiplicity of infection of 0.001. Upon complete lysis of the cells (approximately eight days later), the spent medium was clarified by low speed centrifugation. The supernatant was applied to a rat monoclonal anti-mC$\kappa$-coupled Sepharose column (purchased from Zymed or prepared using rat monoclonal 187.1) equilibrated in TBS pH 7.0. The column was washed with TBS pH 7.0, and the bound mC$_\kappa$ fusion protein eluted in glycine buffer pH 2.2 and neutralized by the addition of 2M Tris pH 8.0. Yields of 2 mg of mC$_\kappa$ fusion protein per liter of cells were obtained.

Results

MAdCAM-1/mC$_\kappa$ fusion protein was expressed under the transcriptional regulation of the viral polyhedrin promoter. To transfer the chimeric gene into the baculovirus genome, pVL941/MAdCAM-1/mC$_\kappa$ plasmid was co-transfected with A. californica nuclear polyhedrosis virus DNA into Sf9 insect cells. Several recombinant plaques were isolated and one was chosen for more detailed characterization.

ELISA assays on Transfected Cell Supernatants

To determine if an ELISA assay could be used to detect the appearance of fusion protein in the supernatant of transfected cells, aliquots (500 $\mu$l) were taken from the supernatant of transfected cells at 3, 4 and 5 days post-transfection, and ELISA assays were performed as described above. The results indicated that the sensitivity of the ELISA assay was sufficient to detect the mC$_\kappa$ fusion protein. The assay can be used to provide an indication that the desired gene is expressed in the insect cells. Moreover, a positive signal in the ELISA assay correlated well with the isolation of recombinant viral particles in subsequent plaque assays.

Cellular Adhesion Assay

The following buffers and reagents were used in the initial titration of capture antibody and in the adhesion inhibition assays:

TABLE 1

CARBONATE BUFFER:

| | | | |
|---|---|---|---|
| 17.2 g NaHCO₃ | | Sigma | #S-8875 |
| 8.6 g Na2CO₃ | | Sigma | #S-6139 |
| Bring volume to 1 L with H2O | | | |

1% BSA/PBS

| | | | |
|---|---|---|---|
| BSA | 5 g | Sigma | #A-6793 |
| PBS | 500 ml | Gibco | #14040-026 |
| Sterile filter | | | |

ASSAY BUFFER
(HBSS/2% FCS/25 mM HEPES/
Pen. Strep., pH 7.2):

| | | | |
|---|---|---|---|
| HBSS | 500 ml | Gibco | #14025-02 |
| FCS | 10 ml | Gibco | #16000-044 |
| HEPES (1M) | 12.5 ml | Gibco | #15630-015 |
| Pen. Strep. (100x) | 5 ml | Gibco | #15070-022 |
| Sterile filter | | | |

2x ASSAY BUFFER (2x
HBSS/4% FCS/50 mM
HEPES/Pen. Strep, pH 7.2):

| | | | |
|---|---|---|---|
| 10x HBSS | 100 ml | Gibco | #14065-023 |
| FCS | 20 ml | Gibco | #16000-044 |
| HEPES(1M) | 25 ml | Gibco | #15630-015 |
| NaHCO₃(7.5%) | 4.7 ml | Gibco | #25080 |
| Pen. Strep. | 10 ml | Gibco | #15070-022 |
| Check pH | | | |
| Bring volume up to 500 ml with H2O | | | |
| Sterile filter | | | |
| BCECF-AM | | Molecular Probes | #B-1170 |
| DMSO | | Sigma | #D-8779 |

Maintenance and Labelling of Cells

HUT 78 cells (a human T cell lymphoma line; American Type Culture Collection, Accession No. ATCC TIB 161) were maintained in culture for up to one month in RPMI 1640 supplemented with 10% FCS, 20 mM HEPES, and Pen-Strep (1:100). Just prior to use in adhesion assays, cells were labeled with BCECF-AM as follows: $1 \times 10^7$ cells were pelleted at 1000 rpm for 10 minutes and resuspended in 25 mL cold PBS (Phosphate Buffered Saline). The cells were pelleted again, resuspended in cold PBS, and pelleted again. The cell pellet was resuspended in 25 ml PBS and labeled with 50 μl BCECF-AM (1 μg/μL in DMSO) for 30 minutes at 37° C. (BCECF-AM; 2',7'-bis-(2-carboxyethyl)-5- (and -6)-carboxyflourescein, acetoxymethyl ester). The labeled cells were pelleted at 700 rpm for 10 minutes, resuspended in 25 ml cold Assay Buffer and pelleted. Finally, labeled cells were counted and resuspended in Assay Buffer (ambient temperature) at a concentration of $2.5 \times 10^6$/ml.

Titration of Capture Antibody

A rat anti-mCκ antibody (affinity purified rat-anti-mC$_K$ monoclonal antibodies from rat hybridoma cell line 187.1; ATCC Accession No. HB58) was selected for use as capture antibody in the adhesion assay. A titration experiment was conducted in order to determine the optimal capture antibody concentration. Assay Buffer for the titration was 2x Assay Buffer.

ELISA plates were coated with various concentrations capture antibody by adding 10 μg/ml, 5 μg/ml, 2.5 μg/ml, or 1.25 μg/ml of antibody in a 50 μl volume to each well and incubating at 4° C. overnight. The next day, plates were blocked with 100 μl 1% BSA/PBS at 37° C. for 1 hour. After one hour, the BSA/PBS solution was removed, and 50 μl MAdCAM-mCκ fusion protein (neat supernatant) was added to each well and incubated for 1 hour at 37° C.

Anti-murine MAdCAM-1 antibody MECA-367 (American Type Culture Collection, Accession No. ATCC HB 9478) was used as a blocking antibody. For the titration, either 20 μl of Assay Buffer (i.e., 2x Assay Buffer), 20 μl of neat supernatant containing anti-MAdCAM-1 MECA-367 antibody, or 20 μl of neat supernatant containing MECA-367 diluted 1:2, 1:4, 1:8 or 1:16 in Assay Buffer, was added to each well. The undiluted supernatant contained approximately 3 μg/ml of antibody.

Frozen BCECF-labeled HUT 78 cells were thawed and resuspended in Assay Buffer at $2.5 \times 10^6$ cells/ml. 50 μl of cells, 50 μl of Assay Buffer (without Pen/Strep), 30 μl of water, 50 μl of 8 mM MnCl₂, and 20 μl of either MECA-367 antibody (neat or diluted) or 20 μl of Assay Buffer alone, were then added to each well, and the plates were incubated on a rotator for 30 minutes at room temperature.

After incubation, a baseline measurement for each well of total fluorescence was taken using a Fluorescence Concentration Analyzer (IDEXX) at 485/535 nM. Then plates were washed twice with a solution of 50 mM Tris/2 mM MnCl₂ using an EL 404 Microplate Autowasher (BIO-TEK Instruments), and fluorescence (due to adherent cells) was determined again using a Fluorescence Concentration Analyzer (IDEXX) at 485/535 nM. For each well, the final reading was divided by the baseline reading. The values from duplicate wells were averaged, and plotted (FIG. 1). Accordingly, 50 μl of a 5 μg/mL solution of rat anti-mCκ was used to coat each well for subsequent adhesion assays.

Inhibition Assays and IC$_{50}$ Determination

The assay was performed in a 96-well format. Plates were coated overnight at 4° C. with 50 μl/well of a 5 μg/mL solution of rat anti-mCκ in carbonate buffer. The plates were blocked for 1 hour at 37° C. with 100 μL/well of 1% BSA in PBS. The BSA/PBS solution was removed, and 50 μL of MAdCAM-mCκ supernatant was added neat to each well. The assay was conducted under conditions in which capture antibody was the limiting reagent.

Cell adhesion was measured in the presence or absence of compounds. The compounds were resuspended in 100% DMSO, subsequently diluted 1:10 in water, and finally diluted again 1:10 in the assay: 50 μL of 2x Assay Buffer, 30 μL water, 20 μL of compound were added to each well. 50 μL of a cell suspension containing BCECF-AM labeled HUT 78 cells (resuspended in assay buffer at a concentration of $2.5 \times 10^6$/ml; see above) were added to each well, followed by 50 μL of a solution of 8 mM MnCl₂ in assay buffer. Cell adhesion occurred in 30 minutes at ambient temperature, after which plates were washed with 50 mM Tris/2 mM MnCl₂, pH 7.2 using an EL 404 Microplate Autowasher (BIO-TEK Instruments) using the following wash parameters: wash volume=500 μL; two wash cycles; wash depth= 80; aspirating after each wash. Plates were read using a Fluorescence Concentration Analyzer (IDEXX) at 485/535 nM.

IC$_{50}$ Determinations

In order to determine an IC$_{50}$ (the concentration of compound which inhibits 50% of the total number of cells adhering to MAdCAM-1 relative to a control conducted in the absence of inhibitor), compounds were tested for inhibition of HUT 78 cell adhesion as described above at various concentrations ranging between ~62.5 to 500 μM. Additional determinations were conducted as needed, so that each IC$_{50}$ was determined over a range which encompassed the IC$_{50}$. Over this range, four different concentrations were tested in duplicate. For example, compound 793-1a was tested at four different concentrations (50 μM, 25 μM, 12.5 μM and 6.25 μM) in duplicate wells.

Figure 2:
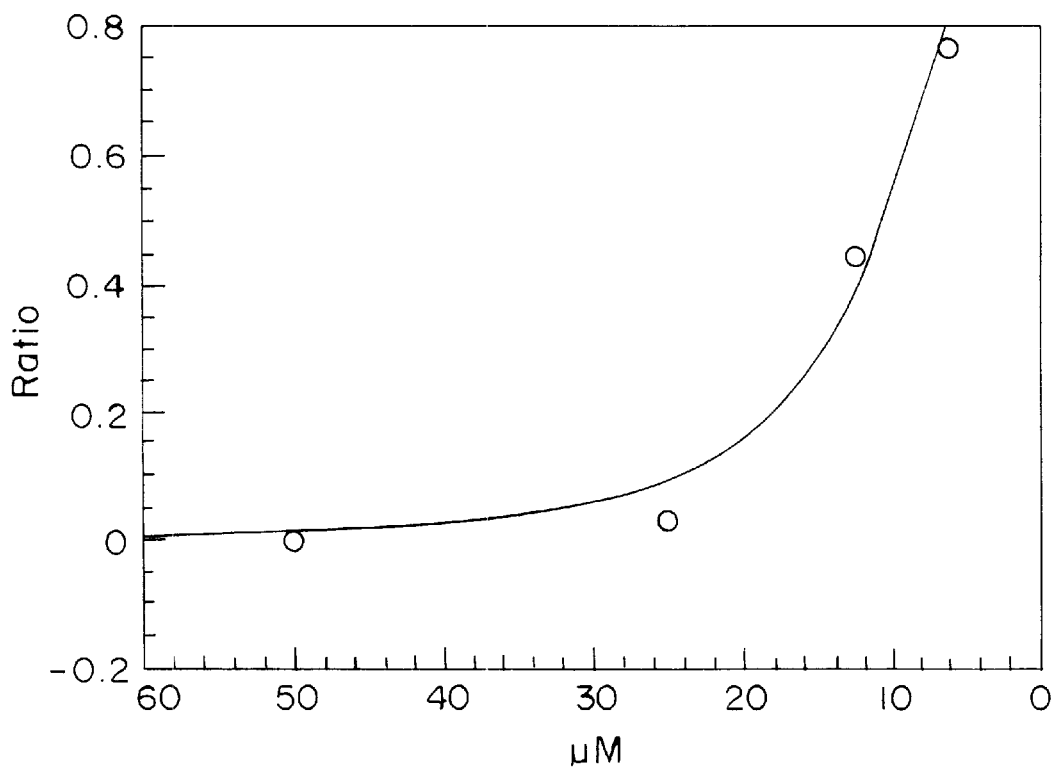
FIG. 2 is a graph illustrating the inhibition by compound 793-1a of the adherence of fluorescently labelled cells bearing α4β7 (HUT 78 human T cell lymphoma cells) to a MAdCAM-mCκ fusion protein bound by capture antibody. The various concentrations (μM) of compound used were plotted against a ratio (calculated from measurements of adherent fluorescent cells; see Example 2).

For each compound, a ratio was determined as follows: An average of the readings from duplicate wells was divided by an average of eight control wells (adhesion in the absence of any compound). Percent inhibition of adhesion was calculated as 100×(1−the ratio). In addition, the concentration ($\mu$M) of compound used was plotted against the resulting ratios. The resulting plot for compound 793-1a is shown in FIG. 2.

The $IC_{50}$ was then determined using Kaleidograph software (Abelbeck Software). The complete procedure was repeated again using duplicate wells for each point. An average of two $IC_{50}$ determinations was obtained, and the resulting values are presented in Table 2 with percent adhesion inhibition for a variety of compounds of the present invention. For example, the $IC_{50}$ for compound 793-1a was determined to be 14 $\mu$M. Cysteines in cyclic peptides which are linked by a disulfide bond are indicated by an "*". Abbreviations used are defined in Table 3 below.

In Table 2, Example No. 1 is represented by SEQ ID NO: 7; Example No. 2 is represented by SEQ ID NO: 8; Example No. 3 is represented by SEQ ID NO: 9; Example No. 4 is represented by SEQ ID NO: 10; Example No. 5 is represented by SEQ ID NO: 11; Example No. 6 is represented by SEQ ID NO: 12; Example No. 7 is represented by SEQ ID NO: 13; Example No. 8 is represented by SEQ ID NO: 14; Example No. 9 is represented by SEQ ID NO: 15; Example No. 10 is represented by SEQ ID NO: 7; Example No. 11 is represented by SEQ ID NO: 16; Example No. 12 is represented by SEQ ID NO: 17; Example No. 13 is represented by SEQ ID NO: 18; Example No. 14 is represented by SEQ ID NO: 9; Example No. 15 is represented by SEQ ID NO: 13; Example No. 16 is represented by SEQ ID NO: 19; Example No. 17 is represented by SEQ ID NO: 20; Example No. 18 is represented by SEQ ID NO: 21; Example No. 19 is represented by SEQ ID NO: 22; Example No. 20 is represented by SEQ ID NO: 23; Example No. 21 is represented by SEQ ID NO: 24; Example No. 22 is represented by SEQ ID NO: 25; Example No. 23 is represented by SEQ ID NO: 26; Example No. 24 is represented by SEQ ID NO: 7; Example No. 25 is represented by SEQ ID NO: 27; Example No. 26 is represented by SEQ ID NO: 28; Example No. 27 is represented by SEQ ID NO: 29; Example No. 28 is represented by SEQ ID NO: 30; Example No. 29 is represented by SEQ ID NO: 31; Example No. 30 is represented by SEQ ID NO: 32; Example No. 31 is represented by SEQ ID NO: 33; Example No. 32 is represented by SEQ ID NO: 34; Example No. 33 is represented by SEQ ID NO: 35; Example No. 34 is represented by SEQ ID NO: 36; Example No. 35 is represented by SEQ ID NO: 37; Example No. 36 is represented by SEQ ID NO: 38; Example No. 37 is represented by SEQ ID NO: 39; Example No. 38 is represented by SEQ ID NO: 40; Example No. 39 is represented by SEQ ID NO: 41; Example No. 40 is represented by SEQ ID NO: 42; Example No. 41 is represented by SEQ ID NO: 43; Example No. 42 is represented by SEQ ID NO: 44; Example No. 43 is represented by SEQ ID NO: 45; Example No. 44 is represented by SEQ ID NO: 46; Example No. 45 is represented by SEQ ID NO: 47; Example No. 46 is represented by SEQ ID NO: 48; Example No. 47 is represented by SEQ ID NO: 49; Example No. 48 is represented by SEQ ID NO: 50; Example No. 49 is represented by SEQ ID NO: 51; Example No. 50 is represented by SEQ ID NO: 52; Example No. 51 is represented by SEQ ID NO: 53; Example No. 54 is represented by SEQ ID NO: 54; Example No. 55 is represented by SEQ ID NO: 55; Example No. 56 is represented by SEQ ID NO: 56; Example No. 57 is represented by SEQ ID NO: 57; Example No. 58 is represented by SEQ ID NO: 7; Example No. 59 is represented by SEQ ID NO: 58; Example No. 60 is represented by SEQ ID NO: 59; Example No. 61 is represented by SEQ ID NO: 60; Example No. 62 is represented by SEQ ID NO: 61.

TABLE 2

| Ex No | L# | Sequence | Method prep | MH+ Cal. | MH+ Found | % Purity HPLC | % Adhesion Inhibition 500 $\mu$M | IC50 ($\mu$M) |
|---|---|---|---|---|---|---|---|---|
| 1 | 00112-1A | Ac—Leu—Asp—Thr—Ser—Leu | B | 591 | 616 | 75 | | 278 |
| 2 | 00619-1A | Ac—Leu—Asp—Ala—Ser—Leu | B | 557 | 563 | 78 | 47 | 1004 |
| 3 | 0092-1A | Ac—His—Trp—Arg—Gly—Leu—Asp | B | 926 | 926 | 50 | 49 | 584 |
| 4 | 00167-1B | Ac—Cys*—Leu—Asp—Thr—Ser—Leu—Cys* | B, D | 797 | 816 | 67 | 51 (@ 250 $\mu$M) | 102.4 |
| 5 | 00145-1B | Ac—Cys*—Gly—Leu—Asp—Thr—Ser—Leu—Gly—Cys* | B, D | 909 | 925 | 80 | 45 (@ 200 $\mu$M) | 266 |
| 6 | 0093-1A | Ac—Trp—Arg—Gly—Leu—Asp—Thr—Ser | B | 877 | 878 | 42 | 44 | 862 |
| 7 | 0096-1A | Ac—Trp—Arg—Gly—Leu—Asp—Thr | B | 789 | 792 | 53 | 46 | 725 |
| 8 | 0094-1A | Ac—Arg—Gly—Leu—Asp—Thr—Ser—Leu | B | 804 | 802 | 34, 41 | 35 | 1575 |
| 9 | 0099-1A | Ac—Gly—Leu—Asp—Thr—Ser—Leu | B | 648 | 647 | 67 | 58 | 339 |
| 10 | 0104-1A | Ac—Leu—Asp—Thr—Ser—Leu | B | 591 | 616 | 47 | 50 | 530 |
| 11 | 0093-1A | Ac—Trp—Arg—Gly—Leu—Asp—Thr—Ser | B | 877 | 878 | 42 | 44 | 862 |
| 12 | 0097-1A | Ac—Arg—Gly—Leu—Asp—Thr—Ser | B | 691 | 691 | 32, 34 | 31 | 1789 |
| 13 | 0108-1A | Ac—Gly—Leu—Asp—Thr—Ser | B | 535 | 554 | 73 | 43 | 745 |
| 14 | 0092-1A | Ac—His—Trp—Arg—Gly—Leu—Asp—Thr | B | 926 | 926 | 50 | 49 | 584 |
| 15 | 0096-1A | Ac—Trp—Arg—Gly—Leu—Asp—Thr | B | 789 | 792 | 53 | 46 | 725 |
| 16 | 0105-1A | Ac—Arg—Gly—Leu—Asp—Thr | B | 603 | 607 | 45 | 48 | 542 |
| 17 | 00379-1A | Ac—MeLeu—Leu—Asp—Thr—Ser—Leu | B | 965 | 966 | 50 | 28 | 1316 |
| 18 | 00380-1A | Phx—Leu—Asp—Thr—Ser—Leu | B, C | 722 | 722 | | 32 | 818 |
| 19 | 00381-1A | Impa—Leu—Asp—Thr—Ser—Leu | B, C | 736 | 737 | | 44 | 1140 |
| 20 | 00382-1A | Bipa—Leu—Asp—Thr—Ser—Leu | B, C | 742 | 765 | 80 | 54 | 485 |
| 21 | 00383-1A | Npa—Leu—Asp—Thr—Ser—Leu | B, C | 716 | 713 | 38, 48 | 39 | 548 |
| 22 | 00384-1A | Hbz—Leu—Asp—Thr—Ser—Leu | B, C | 750 | 770 | 77 | 51 | 401 |
| 23 | 00386-1A | Pba—Leu—Asp—Thr—Ser—Leu | B, C | 818 | 817 | 94 | 88 (@ 50 $\mu$M) | 2.8 |
| 24 | 00389-1A | Ac—Leu—Asp—Thr—Ser—Leu | B, C | 710 | 711 | 61 | 29 | 205 |
| 25 | 00391-1A | Tpc—Leu—Asp—Thr—Ser—Leu | B, C | 672 | 670 | 88 | 39 | 121 |
| 26 | 00392-1A | Pha—Leu—Asp—Thr—Ser—Leu | B, C | 666 | 693 | 86 | 38 | 2128 |

TABLE 2-continued

| Ex No | L# | Sequence | Method prep | MH+ Cal. | MH+ Found | % Purity HPLC | % Adhesion Inhibition 500 μM | IC50 (μM) |
|---|---|---|---|---|---|---|---|---|
| 27 | 00393-1A | MeLeu—Leu—Asp—Thr—Ser—Leu | B, C | 905 | 928 | 86 | 54 | 256 |
| 28 | 00710-1A | Tpa—Leu—Asp—Thr—Ser—Leu | B, C | 813 | 837 | 74 | | 0.3 |
| 29 | 00711-1A | Paa—Leu—Asp—Thr—Ser—Leu | B, C | 785 | 790 | 81 | | 0.5 |
| 30 | 00781-1A | Pba—Pro—Leu—Asp—Thr—Ser—Leu | B, C | 910 | 912 | 77 | | 47 |
| 31 | 00784-1A | Dpa—Leu—Asp—Thr—Ser—Leu | B, C | 737 | 765 | 87 | | 11 |
| 32 | 00785-1A | Dphb—Leu—Asp—Thr—Ser—Leu | B, C | 799 | 807 | 87 | | 15 |
| 33 | 00786-1A | Flc—Leu—Asp—Thr—Ser—Leu | B, C | 735 | 739 | 71 | | 17 |
| 34 | 00787-1A | Pca—Leu—Asp—Thr—Ser—Leu | B, C | 771 | 799 | 80 | | 2.1 |
| 35 | 00788-1A | Xnc—Leu—Asp—Thr—Ser—Leu | B, C | 751 | 757 | 84 | | 3 |
| 36 | 00789-1A | Pba—Leu—Asp—Thr—Ser—Leu | B, C | 813 | 818 | 81 | | 4 |
| 37 | 00793-1A | Tphp—Leu—Asp—Thr—Ser—Leu | B, C | 823 | 831 | 87 | | 14 |
| 38 | 00795-1A | 2-Anc—Leu—Asp—Thr—Ser—Leu | B, C | 747 | 756 | 63 | | 5.4 |
| 39 | 00603-1A | Pba—Leu—Ala—Thr—Ser—Leu | B, C | 771 | 775 | 84 | 100 (@ 250 μM) | 28 |
| 40 | 00605-1A | Ac—Leu—Phe—Thr—Ser—Leu | B | 623 | 623 | 86 | 29 | 299.7 |
| 41 | 00606-1A | Ac—Leu—Glu—Thr—Ser—Leu | B | 605 | 605 | 85 | 98 | 60.7 |
| 42 | 00610-1A | Pba—Leu—Tyr—Thr—Ser—Leu | B, C | 862 | 867 | 95 | 100 | 30 |
| 43 | 00612-1A | Ac—Leu—Asp—Ser—Ser—Leu | B | 578 | 580 | 86 | 38 | 611.4 |
| 44 | 00613-1A | Ac—Leu—Asp—Thr—Thr—Leu | B | 604 | 609 | 71 | 98 | 100.7 |
| 45 | 00614-1A | Ac—Leu—Asp—Thr—Ser—Phe | B | 625 | 625 | 80 | 86 | 143.9 |
| 46 | 00615-1A | AC—Ile—Asp—Thr—Ser—Leu | B | 591 | 593 | 79 | 17 | 18983 |
| 47 | 00712-1A | AC—Leu—Asp—Val—Ser—Leu | B | 589 | 611 | 93 | | 71 |
| 48 | 00716-1A | Ac—Leu—Asp—HyP—Ser—Leu | B | 599 | 626 | 79 | | 106 |
| 49 | 00718-1A | Ac—MeLeu—Asp—Thr—Ser—Leu | B | 587 | 629 | 65 | | 150 |
| 50 | 00799-1A | Cpc—Asp—Thr—Ser—Leu | B, C | 526 | 532 | 73 | | 8.9 |
| 51 | 00649-1A | Pba—Asp—Thr—Ser—Leu | B, C | 702 | 704 | 85 | 100 (@ 100 μM) | 13.3 |
| 52 | 00800-1A | Pca—Asp—Thr | B, C | 459 | 460 | 76 | | 11 |
| 53 | 00650-1A | Pba—Asp—Thr | B, C | 503 | 505 | 96 | 100 (@ 100 μM) | 13.5 |
| 54 | | NH2—Leu—Asp—Thr—Ser—Leu | | | | | 22 | |
| 55 | | NH2—Trp—Arg—Gly—Leu—Asp—Thr—Ser—Leu—Gly—Ser | | | | | 76 | |
| 56 | | NH2—His—Trp—Arg—Gly—Leu—Asp—Thr—Ser—Leu—Gly—Ser—Val | | | | | 80 | |
| 57 | | NH2—Arg—Val—His—Trp—Arg—Gly—Leu—Asp—Thr—Ser—Leu—Gly—Ser—Val—Gln | | | | | 90 | |
| 58 | | Ac—Leu—Asp—Thr—Ser—Leu | | | | | 71 | |
| 59 | | Ac—Arg—Gly—Leu—Asp—Thr—Ser—Leu—Gly | | | | | 75 | |
| 60 | | Ac—Trp—Arg—Gly—Leu—Asp—Thr—Ser—Leu—Gly—Ser | | | | | 71 | |
| 61 | | Ac—His—Trp—Arg—Gly—Leu—Asp—Thr—Ser—Leu—Gly—Ser—Val | | | | | 71 | |
| 62 | | Ac—Arg—Val—His—Trp—Arg—Gly—Leu—Asp—Thr—Ser—Leu—Gly—Ser—Val—Gln | | | | | 88 | |

TABLE 3

| | | |
|---|---|---|
| Ac | = | acetyl |
| Anc | = | 2 Anthracenecarbonyl |
| Bipa | = | 4-biphenylacetyl |
| Bpc | = | benzofuranecarbonyl |
| Chc | = | cyclohexanecarbonyl |
| Cpa | = | 1-cyclopentylacetyl |
| Cpc | = | cyclopentanecarbonyl |
| DBU | = | diazobicyclo [5,40] undec-7-ene |
| DMF | = | N,N-dimethylformanide |
| Dpa | = | diphenylacety |
| Dphb | = | 3,5-diphenylbenzoyl |
| EDT | = | 1,2-ethanedithiol |
| Fc | = | furanecarbonyl |
| HBTU | = | 2(1-benzotriazolyl-1-yl)-1,1,3,3-tetramethyluronium |
| Hbz | = | 4-heptylbenzoyl |
| Hyp | = | 4-hydroxyproline |
| Idc | = | Indolecarbonyl |
| Impa | = | 4-isobutyl-a-methylphenylacetyl |
| Indc | = | Indanecarbonyl |
| NMM | = | N-methylmorpholine |
| Npa | = | a-naphthylacetyl |
| Paa | = | 1-pyreneacetyl |
| Pba | = | 1-pyrenebutyryl |
| Pca | = | 1-pyrenecarbonyl |
| Pha | = | phenylacetyl |
| Phx | = | 6-phenylhexanoyl |
| PYBOP | = | benzotriazolyl-N-oxytripyrrolidinophosphonium-hexafluorophosphate |
| Rink Amide Am Resin | = | 4-[2',4'-dimethoxyphenyl-Fmoc-aminomethyl]-phenoxyacetamido-norlecucylaminomethyl resin |
| Tcc | = | trans-cinnamoyl |
| TFA | = | trifluoroacetic acid |
| Thc | = | Thienylcarbonyl |
| Tpa | = | triphenylacetyl |
| Tpc | = | tetramethylcyclopropylcarbonyl |
| Tphp | = | triphenylpropionyl |
| Xnc | = | xanthenecarbonyl |

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound represented by the following structural formula:

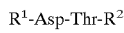
R¹-Asp-Thr-R² wherein:
R¹ is R³—CO—;
R² is —NR⁴R⁵;
R³ is selected from the group consisting of a lower alkyl group, a substituted lower alkyl group, an aryl group, a substituted aryl group, a heteroaryl group and a substituted heteroaryl group, wherein the substituted lower alkyl, substituted aryl or substituted heteroaryl group of R³ is subsituted with one or more substituents selected from the group consisting of: C1–C2 alkoxy, ketone, aldehyde, lower alkyl ester, aryl, substituted aryl, heteroaryl, substituted heteroaryl, benzyl, lower alkyl, halogen, cyano and nitro;
R⁴ and R⁵ are each independently selected from the group consisting of hydrogen, a lower alkyl group, a substituted lower alkyl group, an aryl group, a substituted aryl group, a heteroaryl group and a substituted heteroaryl group, wherein:
1) R⁴ and R⁵ are not both —H; and
2) taken together, R⁴ and R⁵ can form a heterocyclic ring; and the compound has no more than two amino acids.

2. A compound represented by the following structural formula:

R¹-Asp-Thr-R² wherein:
R¹ is R³—CO—;
R² is —NR⁴R⁵;
R³ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indoyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl;
R⁴ and R⁵ are each independently selected from the group consisting of hydrogen, a lower alkyl group, a substituted lower alkyl group, an aryl group, a substituted aryl group, a heteroaryl group and a substituted heteroaryl group, wherein:
1) R⁴ and R⁵ are not both —H; and
2) taken together, R⁴ and R⁵ can form a heterocyclic ring; and the compound has no more than two amino acids.

3. The compound of claim 2 wherein R⁴ and R⁵ are each independently selected from the group consisting of —H, 2-hydroxyethyl, benzyl, 2-benzofuranyl, 3-benzofuranyl, 2-benzothienyl, 3-benzothienyl, —CH₂-2-thienyl, —CH₂-3-thienyl, —CH₂-2-furanyl, —CH₂-3-furanyl, 3,4-dimethoxybenzyl, and isopentyl.

4. A compound represented by the following structural formula:

R¹-Asp-Thr-R² wherein:
R¹ is R³—CO—;
R² is —NR⁴R⁵;
R³ is selected from the group consisting of diphenylmethyl, triphenylmethyl, trans 2-phenylethylenyl, 2-phenyl-ethynyl, 2-benzofuranyl, 3-benzofuranyl, 2-benzothienyl and 3-benzothienyl;
R⁴ is selected from the group consisting of 2-hydroxyethyl, benzyl, 2-benzofuranyl, 3-benzofuranyl, 2-benzothienyl, 3-benzothienyl, —CH₂-2-thienyl, —CH₂-3-thienyl, —CH₂-2-furanyl, —CH₂-3-furanyl; and
R⁵ is —H.

5. A compound represented by the following structural formula:

R¹-Leu-Asp-Thr-R² wherein:
R¹ is R³—CO—;
R² is —NR⁴R⁵;
R³ is selected from the group consisting of a lower alkyl group, a substituted lower alkyl group, an aryl group, a substituted aryl group, a heteroaryl group and a substituted heteroaryl group;
R⁴ and R⁵ are each independently selected from the group consisting of hydrogen, a lower alkyl group, a substituted lower alkyl group, an aryl group, a substituted aryl group, a heteroaryl group and a substituted heteroaryl group, wherein:
1) R⁴ and R⁵ are not both —H; and
2) taken together, R⁴ and R⁵ can form a heterocyclic ring; and the compound has no more than three amino acids.

6. The compound of claim 5 wherein R³ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indoyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl.

7. The compound of claim 6 wherein R⁴ and R⁵ are each independently selected from the group consisting of —H, 2-hydroxyethyl, benzyl, 2-benzofuranyl, 3-benzofuranyl, 2-benzothienyl, 3-benzothienyl, —CH₂-2-thienyl, —CH₂-3-thienyl, —CH₂-2-furanyl, —CH₂-3-furanyl, 3,4-dimethoxybenzyl, and isopentyl.

8. The compound of claim 5 wherein:
R³ is selected from the group consisting of diphenylmethyl, triphenylmethyl, trans 2-phenylethylenyl, 2-phenyl-ethynyl, 2-benzofuranyl, 3-benzofuranyl, 2-benzothienyl and 3-benzothienyl;
R⁴ is selected from the group consisting of 2-hydroxyethyl, benzyl, 2-benzofuranyl, 3-benzofuranyl, 2-benzothienyl, 3-benzothienyl, —CH₂-2-thienyl, —CH₂-3-thienyl, —CH₂-2-furanyl, —CH₂-3-furanyl; and
R⁵ is —H.

9. A method of treating an individual suffering from a disease associated with leukocyte infiltration of tissues expressing the molecule MAdCAM-1, comprising administering a therapeutically effective amount of a compound represented by the following structural formula:

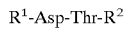

wherein:
R$^1$ is R$^3$—CO—;
R$^2$ is —NR$^4$R$^5$;
R$^3$ is selected from the group consisting of a lower alkyl group, a substituted lower alkyl group, an aryl group, a substituted aryl group, a heteroaryl group and a substituted heteroaryl group, wherein the substituted lower alkyl, substituted aryl or substituted heteroaryl group of R$^3$ is substituted with one or more substituents selected from the group consisting of: C1–C2 alkoxy, ketone, aldehyde, lower alkyl ester, aryl, substituted aryl, heteroaryl, substituted heteroaryl, benzyl, lower alkyl, halogen, cyano and nitro;
R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and
the compound has no more than two amino acids.

10. The method of claim 9 wherein the disease is selected from the group consisting of inflammatory bowel disease and insulin-dependent diabetes mellitus.

11. A method of treating an individual suffering from a disease associated with leukocyte infiltration of tissues expressing the molecule MAdCAM-1, comprising administering a therapeutically effective amount of a compound represented by the following structural formula:

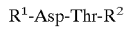

wherein:
R$^1$ is R$^3$—CO—;
R$^2$ is —NR$^4$R$^5$;
R$^3$ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indolyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl;
R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and
the compound has no more than two amino acids.

12. The method of claim 11 wherein R$^4$ and R$^5$ are each independently selected from the group consisting of —H, 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl, 3,4-dimethoxybenzyl, and isopentyl.

13. A method of treating an individual suffering from a disease associated with leukocyte infiltration of tissues expressing the molecule MAdCAM-1, comprising administering a therapeutically effective amount of a compound represented by the following structural formula:

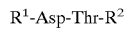

wherein:
R$^1$ is R$^3$—CO—;
R$^2$ is —NR$^4$R$^5$;
R$^3$ is selected from the group consisting of diphenylmethyl, triphenylmethyl, trans 2-phenylethenyl, 2-phenyl-ethynyl, 2-benzofuranyl, 3-benzofuranyl, 2-benzothienyl and 3-benzothienyl;
R$^4$ is selected from the group consisting of 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl;
and R$^5$ is —H.

14. A method of inhibiting the binding of a cell expressing a ligand for MAdCAM-1 on the cell surface to MAdCAM-1 or a portion thereof, comprising contacting the cell with an effective amount of a compound represented by the following structural formula:

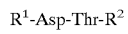

wherein:
R$^1$ is R$^3$—CO—;
R$^2$ is —NR$^4$R$^5$;
R$^3$ is selected from the group consisting of a lower alkyl group, a substituted lower alkyl group, an aryl group, a substituted aryl group, a heteroaryl group and a substituted heteroaryl group, wherein the substituted lower alkyl, substituted aryl or substituted heteroaryl group of R$^3$ is substituted with one or more substituents selected from the group consisting of: C1–C2 alkoxy, ketone, aldehyde, lower alkyl ester, aryl, substituted aryl, heteroaryl, substituted heteroaryl, benzyl, lower alkyl, halogen, cyano and nitro;
R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and
the compound has no more than two amino acids.

15. The method of claim 14 wherein the ligand is human α4β7 integrin.

16. The method of claim 15 wherein the cell is a leukocyte.

17. The method of claim 16 wherein MAdCAM-1 is expressed on the surface of an endothelial cell.

18. A method of inhibiting the binding of a cell expressing a ligand for MAdCAM-1 on the cell surface to MAdCAM-1 or a portion thereof, comprising contacting the cell with an effective amount of a compound represented by the following structural formula:

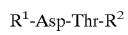

wherein:

R$^1$ is R$^3$—CO—;

R$^2$ is —NR$^4$R$^5$;

R$^3$ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indolyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl;

R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and the compound has no more than two amino acids.

19. The method of claim 18 wherein R$^4$ and R$^5$ are each independently selected from the group consisting of —H, 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl, 3,4-dimethoxybenzyl, and isopentyl.

20. A method of inhibiting the binding of a cell expressing a ligand for MAdCAM-1 on the cell surface to MAdCAM-1 or a portion thereof, comprising contacting the cell with an effective amount of a compound represented by the following structural formula:

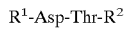

R$^1$-Asp-Thr-R$^2$ wherein:

R$^1$ is R$^3$—CO—;

R$^2$ is —NR$^4$R$^5$;

R$^3$ is selected from the group consisting of diphenylmethyl, triphenylmethyl, trans 2-phenyl-ethylenyl, 2-phenyl-ethynyl, 2-benzofuranyl, 3-benzofuranyl, 2-benzothienyl and 3-benzothienyl;

R$^4$ is selected from the group consisting of 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl; and R$^5$ is —H.

21. A method of treating an individual suffering from a disease associated with leukocyte infiltration of tissues expressing the molecule MAdCAM-1, comprising administering a therapeutically effective amount of a compound represented by the following structural formula:

R$^1$-Leu-Asp-Thr-R$^2$ wherein:

R$^1$ is R$^3$—CO—;

R$^2$ is —NR$^4$R$^5$;

R$^3$ is selected from the group consisting of a lower alkyl, substituted lower alkyl, aryl, substituted aryl, heteroaryl and substituted heteroaryl;

R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and the compound has no more than three amino acids.

22. The method of claim 21 wherein R$^3$ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracene, methyl, cyclopentyl, 2-indoyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl.

23. The method of claim 22 wherein R$^4$ and R$^5$ are each independently selected from the group consisting of —H, 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl, 3,4-dimethoxybenzyl, and isopentyl.

24. The method of claim 21 wherein:

R$^3$ is selected from the group consisting of diphenylmethyl, triphenylmethyl, trans 2-phenyl-ethylenyl, 2-phenyl-ethynyl, 2 benzofuranyl, 3-benzofuranyl, 2-benzothienyl and 3-benzothienyl;

R$^4$ is selected from the group consisting of 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl;

and R$^5$ is —H.

25. The method of claim 21 wherein the disease is selected from the group consisting of inflammatory bowel disease and insulin-dependent diabetes mellitus.

26. A method of inhibiting the binding of a cell expressing a ligand for MAdCAM-1 on the cell surface to MAdCAM-1 or a portion thereof, comprising contacting the cell with an effective amount of a compound represented by the following structural formula:

R$^1$-Leu-Asp-Thr-R$^2$ wherein:

R$^1$ is R$^3$—CO—;

R$^2$ is —NR$^4$R$^5$;

R$^3$ is selected from the group consisting of a lower alkyl, substituted lower alkyl, aryl, substituted aryl, heteroaryl and substituted heteroaryl;

R$^4$ and R$^5$ are each independently selected from the group consisting of hydrogen, a lower alkyl group, a substituted lower alkyl group, an aryl group, a substituted aryl group, a heteroaryl group and a substituted heteroaryl group, wherein:
1) R$^4$ and R$^5$ are not both —H; and
2) taken together, R$^4$ and R$^5$ can form a heterocyclic ring; and the compound has no more than three amino acids.

27. The method of claim 26 wherein the ligand is human α4β7 integrin.

28. The method of claim 27 wherein the cell is a leukocyte.

29. The method of claim 28 wherein MAdCAM-1 is expressed on the surface of an endothelial cell.

30. The method of claim 26 wherein $R^3$ is selected from the group consisting of triphenylmethyl, diphenylmethyl, 3,5-diphenylphenyl, 2-furanyl, 3-furanyl, 9-xanthenemethyl, 2,2,2-triphenylethyl, 2-anthracenemethyl, cyclopentyl, 2-indoyl, 2-indanyl, 2-benzofuranyl, 3-benzofuranyl, 2-benzothienyl, 3-benzothienyl, cyclohexyl, 5-phenylpentyl, 4-isobutyl-α-methylphenylmethyl, 4-biphenylmethyl, α-naphthylmethyl, 4-heptylphenyl, phenylmethyl, trans 2-phenylethenyl and 2,2,3,3-tetramethylcyclopropyl.

31. The method of claim 30 wherein $R^4$ and $R^5$ are each independently selected from the group consisting of —H, 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl, 3,4-dimethoxybenzyl, and isopentyl.

32. The method of claim 26 wherein:

$R^3$ is selected from the group consisting of diphenylmethyl, triphenylmethyl, trans 2-phenyl-ethylenyl, 2-phenyl-ethynyl, 2-benzofuranyl, 3-benzofuranyl, 2-benzothienyl and 3-benzothienyl;

$R^4$ is selected from the group consisting of 2-hydroxyethyl, benzyl, 2-benzofuranyl, 3-benzofuranyl, 2-benzothienyl, 3-benzothienyl, —CH$_2$-2-thienyl, —CH$_2$-3-thienyl, —CH$_2$-2-furanyl, —CH$_2$-3-furanyl; and $R^5$ is —H.

* * * * *

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Leu Asp Thr Ser Leu
1               5

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO:2:

Lys Leu Asp Thr Ser Leu Asp
1               5

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:3:

GGATCCGCTG ATGCTGCACC AACTGTATTC                                    30

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:4:

CCTTTGTCCT AACACTCATT CCTGTT                                        26

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

GATCAGGGAT CCATGGAATC CATCCTGGCC CTCCTG                             36

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:6:

TCGATCGGAT CCGGTGGAGG AGGAATTCGG GGTCA                35

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:7:

Leu Asp Thr Ser Leu
1           5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:8:

Leu Asp Ala Ser Leu
1           5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide

```
        (ix) FEATURE:
              (A) NAME/KEY: Modified-site
              (B) LOCATION: 1
              (D) OTHER INFORMATION: /label= modified aa
                    /note= "Ac - Histidine"

(ix) FEATURE:
              (A) NAME/KEY: Modified-site
              (B) LOCATION: 7
              (D) OTHER INFORMATION: /label= modified aa
                    /note= "Threonine-NH2"

(xi) SEQUENCE DESCRIPTION: SEQ ID NO:9:

His Trp Arg Gly Leu Asp Thr
1               5

(2) INFORMATION FOR SEQ ID NO:10:

(i) SEQUENCE CHARACTERISTICS:
              (A) LENGTH: 7 amino acids
              (B) TYPE: amino acid
              (C) STRANDEDNESS:
              (D) TOPOLOGY: circular (ii) MOLECULE TYPE: peptide (ix) FEATURE:
              (A) NAME/KEY: Modified-site
              (B) LOCATION: 1
              (D) OTHER INFORMATION: /label= modified aa
                    /note= "Ac - Cysteine"

(ix) FEATURE:
              (A) NAME/KEY: Modified-site
              (B) LOCATION: 7
              (D) OTHER INFORMATION: /label= modified aa
                    /note= "cysteine - NH2"

(xi) SEQUENCE DESCRIPTION: SEQ ID NO:10:

Cys Leu Asp Thr Ser Leu Cys
1               5

(2) INFORMATION FOR SEQ ID NO:11:

(i) SEQUENCE CHARACTERISTICS:
              (A) LENGTH: 9 amino acids
              (B) TYPE: amino acid
              (C) STRANDEDNESS:
              (D) TOPOLOGY: circular (ii) MOLECULE TYPE: peptide (ix) FEATURE:
              (A) NAME/KEY: Modified-site
              (B) LOCATION: 1
              (D) OTHER INFORMATION: /label= modified aa
                    /note= "Ac - cysteine"

(ix) FEATURE:
              (A) NAME/KEY: Modified-site
              (B) LOCATION: 9
              (D) OTHER INFORMATION: /label= modified aa
                    /note= "cysteine - NH2"

(xi) SEQUENCE DESCRIPTION: SEQ ID NO:11:

Cys Gly Leu Asp Thr Ser Leu Gly Cys
1               5

(2) INFORMATION FOR SEQ ID NO:12:

(i) SEQUENCE CHARACTERISTICS:
              (A) LENGTH: 7 amino acids
              (B) TYPE: amino acid
```

(C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label= modified aa
                    /note= "Ac - tryptophan"

(ix) FEATURE:
                (A) NAME/KEY: Modified-site
                (B) LOCATION: 7
                (D) OTHER INFORMATION: /label= modified aa
                    /note= "Serine - NH2"

(xi) SEQUENCE DESCRIPTION: SEQ ID NO:12:

Trp Arg Gly Leu Asp Thr Ser
1               5

(2) INFORMATION FOR SEQ ID NO:13:

(i) SEQUENCE CHARACTERISTICS:
                (A) LENGTH: 6 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label= modified aa
                    /note= "Ac - Tryptophan"

(ix) FEATURE:
                (A) NAME/KEY: Modified-site
                (B) LOCATION: 6
                (D) OTHER INFORMATION: /label= modified aa
                    /note= "Threonine - NH2"

(xi) SEQUENCE DESCRIPTION: SEQ ID NO:13:

Trp Arg Gly Leu Asp Thr
1               5

(2) INFORMATION FOR SEQ ID NO:14:

(i) SEQUENCE CHARACTERISTICS:
                (A) LENGTH: 7 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /label= modified aa
                    /note= "Ac - Arginine"

(ix) FEATURE:
                (A) NAME/KEY: Modified-site
                (B) LOCATION: 7
                (D) OTHER INFORMATION: /label= modified aa
                    /note= "Leucine - NH2"

(xi) SEQUENCE DESCRIPTION: SEQ ID NO:14:

Arg Gly Leu Asp Thr Ser Leu
1               5

-continued

```
(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modifed aa
            /note= "Ac - Glycine"

(ix) FEATURE:
        (A) NAME/KEY: Modified-site
        (B) LOCATION: 6
        (D) OTHER INFORMATION: /label= modified aa
            /note= "Leucine - NH2"

(xi) SEQUENCE DESCRIPTION: SEQ ID NO:15:

Gly Leu Asp Thr Ser Leu
1               5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Tryptophan"

(ix) FEATURE:
        (A) NAME/KEY: Modified-site
        (B) LOCATION: 7
        (D) OTHER INFORMATION: /label= modified aa
            /note= "Serine - NH2"

(xi) SEQUENCE DESCRIPTION: SEQ ID NO:16:

Trp Arg Gly Leu Asp Thr Ser
1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Arginine"

(ix) FEATURE:
        (A) NAME/KEY: Modified-site
        (B) LOCATION: 6
        (D) OTHER INFORMATION: /label= modified aa
            /note= "Serine - NH2"

(xi) SEQUENCE DESCRIPTION: SEQ ID NO:17:
```

```
Arg Gly Leu Asp Thr Ser
1               5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Glycine"

(ix) FEATURE:
        (A) NAME/KEY: Modified-site
        (B) LOCATION: 5
        (D) OTHER INFORMATION: /label= modified aa
            /note= "Serine - NH2"

(xi) SEQUENCE DESCRIPTION: SEQ ID NO:18:

Gly Leu Asp Thr Ser
1               5

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Arginine"

(ix) FEATURE:
        (A) NAME/KEY: Modified-site
        (B) LOCATION: 5
        (D) OTHER INFORMATION: /label= modified aa
            /note= "Threonine - NH2"

(xi) SEQUENCE DESCRIPTION: SEQ ID NO:19:

Arg Gly Leu Asp Thr
1               5

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Xaa - acetyl N-methylleucine"

(ix) FEATURE:
        (A) NAME/KEY: Modified-site
```

(B) LOCATION: 6
            (D) OTHER INFORMATION: /label= modified aa
                /note= "Leucine - NH2"

(xi) SEQUENCE DESCRIPTION: SEQ ID NO:20:

Xaa Leu Asp Thr Ser Leu
1               5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Phx - Leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:21:

Leu Asp Thr Ser Leu
1               5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Impa - Leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:22:

Leu Asp Thr Ser Leu
1               5

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1

(D) OTHER INFORMATION: /label= modified aa
                /note= "Bipa - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:23:

Leu Asp Thr Ser Leu
1               5

(2) INFORMATION FOR SEQ ID NO:24:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Npa - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:24:

Leu Asp Thr Ser Leu
1               5

(2) INFORMATION FOR SEQ ID NO:25:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Hbz - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:25:

Leu Asp Thr Ser Leu
1               5

(2) INFORMATION FOR SEQ ID NO:26:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Pba - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:26:

Leu Asp Thr Ser Leu
1               5

(2) INFORMATION FOR SEQ ID NO:27:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Tpc - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:27:

Leu Asp Thr Ser Leu
1               5

(2) INFORMATION FOR SEQ ID NO:28:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Pha - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:28:

Leu Asp Thr Ser Leu
1               5

(2) INFORMATION FOR SEQ ID NO:29:

(i) SEQUENCE CHARACTERISTICS:

```
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Xaa - Acetyl-N-methylleucine"

(ix) FEATURE:
            (A) NAME/KEY: Modified-site
            (B) LOCATION: 6
            (D) OTHER INFORMATION: /label= modified aa
                /note= "leucine-NH2"

(xi) SEQUENCE DESCRIPTION: SEQ ID NO:29:

Xaa Leu Asp Thr Ser Leu
1               5

(2) INFORMATION FOR SEQ ID NO:30:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Tpa - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:30:

Leu Asp Thr Ser Leu
1               5

(2) INFORMATION FOR SEQ ID NO:31:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Paa - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:31:

Leu Asp Thr Ser Leu
1               5
```

```
(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Pba - Proline"

(ix) FEATURE:
        (A) NAME/KEY: Modified-site
        (B) LOCATION: 6
        (D) OTHER INFORMATION: /label= modified aa
            /note= "Leucine - NH2"

(xi) SEQUENCE DESCRIPTION: SEQ ID NO:32:

Pro Leu Asp Thr Ser Leu
1               5

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Dpha - Leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:33:

Leu Asp Thr Ser Leu
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Dphb - Leucine"

(ix) FEATURE:
        (A) NAME/KEY: Modified-site
        (B) LOCATION: 5
        (D) OTHER INFORMATION: /label= modified aa
            /note= "Leucine - NH2"
```

```
        (xi) SEQUENCE DESCRIPTION: SEQ ID NO:34:

Leu Asp Thr Ser Leu
1               5

(2) INFORMATION FOR SEQ ID NO:35:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= modified aa
              /note= "Flc - Leucine"

(ix) FEATURE:
          (A) NAME/KEY: Modified-site
          (B) LOCATION: 5
          (D) OTHER INFORMATION: /label= modified aa
              /note= "Leucine - NH2"

(xi) SEQUENCE DESCRIPTION: SEQ ID NO:35:

Leu Asp Thr Ser Leu
1               5

(2) INFORMATION FOR SEQ ID NO:36:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= modified aa
              /note= "Pca - Leucine"

(ix) FEATURE:
          (A) NAME/KEY: Modified-site
          (B) LOCATION: 5
          (D) OTHER INFORMATION: /label= modified aa
              /note= "Leucine - NH2"

(xi) SEQUENCE DESCRIPTION: SEQ ID NO:36:

Leu Asp Thr Ser Leu
1               5

(2) INFORMATION FOR SEQ ID NO:37:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= modified aa
              /note= "Xnc - Leucine"
```

(ix) FEATURE:
                  (A) NAME/KEY: Modified-site
                  (B) LOCATION: 5
                  (D) OTHER INFORMATION: /label= modified aa
                        /note= "Leucine - NH2"

(xi) SEQUENCE DESCRIPTION: SEQ ID NO:37:

Leu Asp Thr Ser Leu
1               5

(2) INFORMATION FOR SEQ ID NO:38:

(i) SEQUENCE CHARACTERISTICS:
                  (A) LENGTH: 5 amino acids
                  (B) TYPE: amino acid
                  (C) STRANDEDNESS:
                  (D) TOPOLOGY: linear (ii) MOLECULE TYPE: peptide (ix) FEATURE:
                  (A) NAME/KEY: Modified-site
                  (B) LOCATION: 1
                  (D) OTHER INFORMATION: /label= modified aa
                        /note= "Pba - Leucine"

(ix) FEATURE:
                  (A) NAME/KEY: Modified-site
                  (B) LOCATION: 5
                  (D) OTHER INFORMATION: /label= modified aa
                        /note= "Leucine - NH2"

(xi) SEQUENCE DESCRIPTION: SEQ ID NO:38:

Leu Asp Thr Ser Leu
1               5

(2) INFORMATION FOR SEQ ID NO:39:

(i) SEQUENCE CHARACTERISTICS:
                  (A) LENGTH: 5 amino acids
                  (B) TYPE: amino acid
                  (C) STRANDEDNESS:
                  (D) TOPOLOGY: linear (ii) MOLECULE TYPE: peptide (ix) FEATURE:
                  (A) NAME/KEY: Modified-site
                  (B) LOCATION: 1
                  (D) OTHER INFORMATION: /label= modified aa
                        /note= "Tphp - Leucine"

(ix) FEATURE:
                  (A) NAME/KEY: Modified-site
                  (B) LOCATION: 5
                  (D) OTHER INFORMATION: /label= modified aa
                        /note= "Leucine - NH2"

(xi) SEQUENCE DESCRIPTION: SEQ ID NO:39:

Leu Asp Thr Ser Leu
1               5

(2) INFORMATION FOR SEQ ID NO:40:

(i) SEQUENCE CHARACTERISTICS:
                  (A) LENGTH: 5 amino acids
                  (B) TYPE: amino acid
                  (C) STRANDEDNESS:
                  (D) TOPOLOGY: linear (ii) MOLECULE TYPE: peptide (ix) FEATURE:

```
            (A) NAME/KEY: Modified-site
            (B) LOCATION: 1
            (D) OTHER INFORMATION: /label= modified aa
                /note= "2-Anc - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:40:

Leu Asp Thr Ser Leu
1               5

(2) INFORMATION FOR SEQ ID NO:41:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Pba - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:41:

Leu Ala Thr Ser Leu
1               5

(2) INFORMATION FOR SEQ ID NO:42:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Ac - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:42:

Leu Phe Thr Ser Leu
1               5

(2) INFORMATION FOR SEQ ID NO:43:

(i) SEQUENCE CHARACTERISTICS:
            (A) LENGTH: 5 amino acids
            (B) TYPE: amino acid
            (C) STRANDEDNESS:
```

```
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Ac - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:43:

Leu Glu Thr Ser Leu
1               5

(2) INFORMATION FOR SEQ ID NO:44:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Pba - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:44:

Leu Tyr Thr Ser Leu
1               5

(2) INFORMATION FOR SEQ ID NO:45:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Ac - Leucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:45:

Leu Asp Ser Ser Leu
1               5

(2) INFORMATION FOR SEQ ID NO:46:
```

```
    (i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= modified aa
             /note= "Ac - Leucine"

(ix) FEATURE:
         (A) NAME/KEY: Modified-site
         (B) LOCATION: 5
         (D) OTHER INFORMATION: /label= modified aa
             /note= "Leucine - NH2"

(xi) SEQUENCE DESCRIPTION: SEQ ID NO:46:

Leu Asp Thr Thr Leu
1               5

(2) INFORMATION FOR SEQ ID NO:47:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= modified aa
             /note= "Ac - Leucine"

(ix) FEATURE:
         (A) NAME/KEY: Modified-site
         (B) LOCATION: 5
         (D) OTHER INFORMATION: /label= modified aa
             /note= "Phenylalamine - NH2"

(xi) SEQUENCE DESCRIPTION: SEQ ID NO:47:

Leu Asp Thr Ser Phe
1               5

(2) INFORMATION FOR SEQ ID NO:48:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /label= modified aa
             /note= "Ac - Isoleucine"

(ix) FEATURE:
         (A) NAME/KEY: Modified-site
         (B) LOCATION: 5
         (D) OTHER INFORMATION: /label= modified aa
             /note= "Leucine - NH2"

(xi) SEQUENCE DESCRIPTION: SEQ ID NO:48:
```

```
Ile Asp Thr Ser Leu
1               5

(2) INFORMATION FOR SEQ ID NO:49:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Leucine"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:49:

Leu Asp Val Ser Leu
1               5

(2) INFORMATION FOR SEQ ID NO:50:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Leucine"

(ix) FEATURE:
        (A) NAME/KEY: Modified-site
        (B) LOCATION: 3
        (D) OTHER INFORMATION: /label= modified aa
            /note= "4-Hydroxyproline"

(ix) FEATURE:
        (A) NAME/KEY: Modified-site
        (B) LOCATION: 5
        (D) OTHER INFORMATION: /label= modified aa
            /note= "Leucine - NH2"

(xi) SEQUENCE DESCRIPTION: SEQ ID NO:50:

Leu Asp Pro Ser Leu
1               5

(2) INFORMATION FOR SEQ ID NO:51:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
```

(D) OTHER INFORMATION: /label= modified aa
                /note= "Ac - N-methylleucine"

(ix) FEATURE:
            (A) NAME/KEY: Modified-site
            (B) LOCATION: 5
            (D) OTHER INFORMATION: /label= modified aa
                /note= "Leucine - NH2"

(xi) SEQUENCE DESCRIPTION: SEQ ID NO:51:

Xaa Asp Thr Ser Leu
1               5

(2) INFORMATION FOR SEQ ID NO:52:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Cpc - Aspartic acid"

(ix) FEATURE:
            (A) NAME/KEY: Modified-site
            (B) LOCATION: 4
            (D) OTHER INFORMATION: /label= modified aa
                /note= "Leucine - NH2"

(xi) SEQUENCE DESCRIPTION: SEQ ID NO:52:

Asp Thr Ser Leu
1

(2) INFORMATION FOR SEQ ID NO:53:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= modified aa
                /note= "Pba - Aspartic acid"

(ix) FEATURE:
            (A) NAME/KEY: Modified-site
            (B) LOCATION: 4
            (D) OTHER INFORMATION: /label= modified aa
                /note= "Leucine - NH2"

(xi) SEQUENCE DESCRIPTION: SEQ ID NO:53:

Asp Thr Ser Leu
1

(2) INFORMATION FOR SEQ ID NO:54:

(i) SEQUENCE CHARACTERISTICS:
            (A) LENGTH: 5 amino acids
            (B) TYPE: amino acid
            (C) STRANDEDNESS:
            (D) TOPOLOGY: linear

```
    (ii) MOLECULE TYPE: peptide (ix) FEATURE:
         (A) NAME/KEY: Modified-site
         (B) LOCATION: 5
         (D) OTHER INFORMATION: /label= modified aa
             /note= "Leucine - NH2"

(xi) SEQUENCE DESCRIPTION: SEQ ID NO:54:

Leu Asp Thr Ser Leu
1               5

(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 10
         (D) OTHER INFORMATION: /label= modified aa
             /note= "Serine - NH2"

(xi) SEQUENCE DESCRIPTION: SEQ ID NO:55:

Trp Arg Gly Leu Asp Thr Ser Leu Gly Ser
1               5                   10

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 12
         (D) OTHER INFORMATION: /label= modified aa
             /note= "Valine - NH2"

(xi) SEQUENCE DESCRIPTION: SEQ ID NO:56:

His Trp Arg Gly Leu Asp Thr Ser Leu Gly Ser Val
1               5                   10

(2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 15
         (D) OTHER INFORMATION: /label= modified aa
             /note= "Glutamine - NH2"

(xi) SEQUENCE DESCRIPTION: SEQ ID NO:57:

Arg Val His Trp Arg Gly Leu Asp Thr Ser Leu Gly Ser Val Gln
1               5                   10                  15
```

```
(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Arginine"

(ix) FEATURE:
        (A) NAME/KEY: Modified-site
        (B) LOCATION: 8
        (D) OTHER INFORMATION: /label= modified aa
            /note= "Glycine - NH2"

(xi) SEQUENCE DESCRIPTION: SEQ ID NO:58:

Arg Gly Leu Asp Thr Ser Leu Gly
1               5

(2) INFORMATION FOR SEQ ID NO:59:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Tryptophan"

(ix) FEATURE:
        (A) NAME/KEY: Modified-site
        (B) LOCATION: 10
        (D) OTHER INFORMATION: /label= modified aa
            /note= "Serine - NH2"

(xi) SEQUENCE DESCRIPTION: SEQ ID NO:59:

Trp Arg Gly Leu Asp Thr Ser Leu Gly Ser
1               5                   10

(2) INFORMATION FOR SEQ ID NO:60:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Histidine"

(ix) FEATURE:
        (A) NAME/KEY: Modified-site
        (B) LOCATION: 12
        (D) OTHER INFORMATION: /label= modified aa
            /note= "Valine - NH2"
```

(xi) SEQUENCE DESCRIPTION: SEQ ID NO:60:

His Trp Arg Gly Leu Asp Thr Ser Leu Gly Ser Val
1               5                   10

(2) INFORMATION FOR SEQ ID NO:61:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= modified aa
            /note= "Ac - Arginine"

(ix) FEATURE:
        (A) NAME/KEY: Modified-site
        (B) LOCATION: 15
        (D) OTHER INFORMATION: /label= modified aa
            /note= "Glutamic acid - NH2"

(xi) SEQUENCE DESCRIPTION: SEQ ID NO:61:

Arg Val His Trp Arg Gly Leu Asp Thr Ser Leu Gly Ser Val Gln
1               5                   10                  15

(2) INFORMATION FOR SEQ ID NO:62:

(i) SEQUENCE CHARACTERISTICS:
        (A) LENGTH: 5 amino acids
        (B) TYPE: amino acid
        (C) STRANDEDNESS:
        (D) TOPOLOGY: circular (xi) SEQUENCE DESCRIPTION: SEQ ID NO:62:

Leu Asp Thr Ser Leu
1               5

(2) INFORMATION FOR SEQ ID NO:63:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..39

(xi) SEQUENCE DESCRIPTION: SEQ ID NO:63:

CCG AAT TCC TCC TCC ACC GGA TCC GCT GAT GCT GCA CCA            39
Pro Asn Ser Ser Ser Thr Gly Ser Ala Asp Ala Ala Pro
1               5                   10

(2) INFORMATION FOR SEQ ID NO:64:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:64:

Pro Asn Ser Ser Ser Thr Gly Ser Ala Asp Ala Ala Pro (2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 7..21

(xi) SEQUENCE DESCRIPTION: SEQ ID NO:65:

```
GGATTC ATG GAA TCC ATC CTG                                          21
       Met Glu Ser Ile Leu
         1               5
```

(2) INFORMATION FOR SEQ ID NO:66:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:66:

```
Met Glu Ser Ile Leu
  1               5
```

(2) INFORMATION FOR SEQ ID NO:67:

(i) SEQUENCE CHARACTERISTICS:
        (A) LENGTH: 1624 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1218

(xi) SEQUENCE DESCRIPTION: SEQ ID NO:67:

```
ATG GAT TTC GGA CTG GCC CTC CTG CTG GCG GGG CTT CTG GGG CTC CTC      48
Met Asp Phe Gly Leu Ala Leu Leu Leu Ala Gly Leu Leu Gly Leu Leu
  1               5                  10                  15

CTC GGC CAG TCC CTC CAG GTG AAG CCC CTG CAG GTG GAG CCC CCG GAG      96
Leu Gly Gln Ser Leu Gln Val Lys Pro Leu Gln Val Glu Pro Pro Glu
                 20                  25                  30

CCG GTG GTG GCC GTG GCC TTG GGC GCC TCG CGC CAG CTC ACC TGC CGC     144
Pro Val Val Ala Val Ala Leu Gly Ala Ser Arg Gln Leu Thr Cys Arg
             35                  40                  45

CTG GCC TGC GCG GAC CGC GGG GCC TCG GTG CAG TGG CGG GGC CTG GAC     192
Leu Ala Cys Ala Asp Arg Gly Ala Ser Val Gln Trp Arg Gly Leu Asp
         50                  55                  60

ACC AGC CTG GGC GCG GTG CAG TCG GAC ACG GGC CGC AGC GTC CTC ACC     240
Thr Ser Leu Gly Ala Val Gln Ser Asp Thr Gly Arg Ser Val Leu Thr
 65                  70                  75                  80

GTG CGC AAC GCC TCG CTG TCG GCG GCC GGG ACC CGC GTG TGC GTG GGC     288
Val Arg Asn Ala Ser Leu Ser Ala Ala Gly Thr Arg Val Cys Val Gly
                 85                  90                  95

TCC TGC GGG GGC CGC ACC TTC CAG CAC ACC GTG CAG CTC CTT GTG TAC     336
Ser Cys Gly Gly Arg Thr Phe Gln His Thr Val Gln Leu Leu Val Tyr
```

-continued

```
               100                 105                 110
GCC TTC CCG GAC CAG CTG ACC GTC TCC CCA GCA GCC CTG GTG CCT GGT        384
Ala Phe Pro Asp Gln Leu Thr Val Ser Pro Ala Ala Leu Val Pro Gly
        115                 120                 125

GAC CCG GAG GTG GCC TGT ACG GCC CAC AAA GTC ACG CCC GTG GAC CCC        432
Asp Pro Glu Val Ala Cys Thr Ala His Lys Val Thr Pro Val Asp Pro
    130                 135                 140

AAC GCG CTC TCC TTC TCC CTG CTC GTC GGG GGC CAG GAA CTG GAG GGG        480
Asn Ala Leu Ser Phe Ser Leu Leu Val Gly Gly Gln Glu Leu Glu Gly
145                 150                 155                 160

GCG CAA GCC CTG GGC CCG GAG GTG CAG GAG GAG GAG GAG GAG CCC CAG        528
Ala Gln Ala Leu Gly Pro Glu Val Gln Glu Glu Glu Glu Glu Pro Gln
                165                 170                 175

GGG GAC GAG GAC GTG CTG TTC AGG GTG ACA GAG CGC TGG CGG CTG CCG        576
Gly Asp Glu Asp Val Leu Phe Arg Val Thr Glu Arg Trp Arg Leu Pro
            180                 185                 190

CCC CTG GGG ACC CCT GTC CCG CCC GCC CTC TAC TGC CAG GCC ACG ATG        624
Pro Leu Gly Thr Pro Val Pro Pro Ala Leu Tyr Cys Gln Ala Thr Met
        195                 200                 205

AGG CTG CCT GGC TTG GAG CTC AGC CAC CGC CAG GCC ATC CCC GTC CTG        672
Arg Leu Pro Gly Leu Glu Leu Ser His Arg Gln Ala Ile Pro Val Leu
    210                 215                 220

CAC AGC CCG ACC TCC CCG GAG CCT CCC GAC ACC ACC TCC CCG GAG CCT        720
His Ser Pro Thr Ser Pro Glu Pro Pro Asp Thr Thr Ser Pro Glu Pro
225                 230                 235                 240

CCC AAC ACC ACC TCC CCG GAG TCT CCC GAC ACC ACC TCC CCG GAG TCT        768
Pro Asn Thr Thr Ser Pro Glu Ser Pro Asp Thr Thr Ser Pro Glu Ser
                245                 250                 255

CCC GAC ACC ACC TCC CAG GAG CCT CCC GAC ACC ACC TCC CAG GAG CCT        816
Pro Asp Thr Thr Ser Gln Glu Pro Pro Asp Thr Thr Ser Gln Glu Pro
            260                 265                 270

CCC GAC ACC ACC TCC CAG GAG CCT CCC GAC ACC ACC TCC CCG GAG CCT        864
Pro Asp Thr Thr Ser Gln Glu Pro Pro Asp Thr Thr Ser Pro Glu Pro
        275                 280                 285

CCC GAC AAG ACC TCC CCG GAG CCC GCC CCC CAG CAG GGC TCC ACA CAC        912
Pro Asp Lys Thr Ser Pro Glu Pro Ala Pro Gln Gln Gly Ser Thr His
    290                 295                 300

ACC CCC AGG AGC CCA GGC TCC ACC AGG ACT CGC CGC CCT GAG ATC TCC        960
Thr Pro Arg Ser Pro Gly Ser Thr Arg Thr Arg Arg Pro Glu Ile Ser
305                 310                 315                 320

CAG GCT GGG CCC ACG CAG GGA GAA GTG ATC CCA ACA GGC TCG TCC AAA       1008
Gln Ala Gly Pro Thr Gln Gly Glu Val Ile Pro Thr Gly Ser Ser Lys
                325                 330                 335

CCT GCG GGT GAC CAG CTG CCC GCG GCT CTG TGG ACC AGC AGT GCG GTG       1056
Pro Ala Gly Asp Gln Leu Pro Ala Ala Leu Trp Thr Ser Ser Ala Val
            340                 345                 350

CTG GGA CTG CTC CTG GCC TTG CCC ACG TAT CAC CTC TGG AAA CGC           1104
Leu Gly Leu Leu Leu Ala Leu Pro Thr Tyr His Leu Trp Lys Arg
        355                 360                 365

TGC CGG CAC CTG GCT GAG GAC GAC ACC CAC CCA CCA GCT TCT CTG AGG       1152
Cys Arg His Leu Ala Glu Asp Asp Thr His Pro Pro Ala Ser Leu Arg
    370                 375                 380

CTT CTG CCC CAG GTG TCG GCC TGG GCT GGG TTA AGG GGG ACC GGC CAG       1200
Leu Leu Pro Gln Val Ser Ala Trp Ala Gly Leu Arg Gly Thr Gly Gln
385                 390                 395                 400

GTC GGG ATC AGC CCC TCC TGAGTGGCCA GCCTTTCCCC CTGTGAAAGC              1248
Val Gly Ile Ser Pro Ser
                405

AAAATAGCTT GGACCCCTTC AAGTTGAGAA CTGGTCAGGG CAAACCTGCC TCCCATTCTA     1308
```

```
CTCAAAGTCA TCCCTCTGCT CACAGAGATG GATGCATGTT CTGATTGCCT CTTTGGAGAA    1368

GCTCATCAGA AACTCAAAAG AAGGCCACTG TTTGTCTCAC CTACCCATGA CCTGAAGCCC    1428

CTCCCTGAGT GGTCCCCACC TTTCTGGACG GAACCACGTA CTTTTTACAT ACATTGATTC    1488

ATGTCTCACG TCTCCCTAAA AATGCGTAAG ACCAAGCTGT GCCCTGACCA CCCTGGGCCC    1548

CTGTCGTCAG GACCTCCTGA GGCTTTGGCA AATAAACCTC CTAAAATGAT AAAAAAAAAA    1608

AAAAAAAAAA AAAAAA                                                   1624
```

(2) INFORMATION FOR SEQ ID NO:68:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO:68:

```
Met Asp Phe Gly Leu Ala Leu Leu Ala Gly Leu Leu Gly Leu Leu
 1               5                  10                  15

Leu Gly Gln Ser Leu Gln Val Lys Pro Leu Gln Val Glu Pro Glu
                20                  25                  30

Pro Val Ala Val Ala Leu Gly Ala Ser Arg Gln Leu Thr Cys Arg
                35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
 65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
                100                 105                 110

Ala Phe Pro Asp Gln Leu Thr Val Ser Pro Ala Ala Leu Val Pro Gly
                115                 120                 125

Asp Pro Glu Val Ala Cys Thr Ala His Lys Val Thr Pro Val Asp Pro
    130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
    180                 185                 190

Pro Leu Gly Thr Pro Val Pro Pro Ala Leu Tyr Cys Gln Ala Thr Met
                195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Pro
225                 230                 235                 240

Pro Asn Thr Thr Ser Pro Glu Ser Pro Asp Thr Thr Ser Pro Glu Ser
                245                 250                 255

Pro Asp Thr Thr Ser Gln Glu Pro Pro Asp Thr Thr Ser Gln Glu Pro
                260                 265                 270

Pro Asp Thr Thr Ser Gln Glu Pro Pro Asp Thr Thr Ser Pro Glu Pro
                275                 280                 285
```

```
Pro Asp Lys Thr Ser Pro Glu Pro Ala Pro Gln Gln Gly Ser Thr His
    290                 295                 300

Thr Pro Arg Ser Pro Gly Ser Thr Arg Thr Arg Arg Pro Glu Ile Ser
305                 310                 315                 320

Gln Ala Gly Pro Thr Gln Gly Glu Val Ile Pro Thr Gly Ser Ser Lys
                325                 330                 335

Pro Ala Gly Asp Gln Leu Pro Ala Ala Leu Trp Thr Ser Ser Ala Val
            340                 345                 350

Leu Gly Leu Leu Leu Leu Ala Leu Pro Thr Tyr His Leu Trp Lys Arg
            355                 360                 365

Cys Arg His Leu Ala Glu Asp Asp Thr His Pro Pro Ala Ser Leu Arg
        370                 375                 380

Leu Leu Pro Gln Val Ser Ala Trp Ala Gly Leu Arg Gly Thr Gly Gln
385                 390                 395                 400

Val Gly Ile Ser Pro Ser
                405
```

(2) INFORMATION FOR SEQ ID NO:69:

(i) SEQUENCE CHARACTERISTICS:
        (A) LENGTH: 1539 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1146

(xi) SEQUENCE DESCRIPTION: SEQ ID NO:69:

```
ATG GAT TTC GGA CTG GCC CTC CTG CTG GCG GGG CTT CTG GGG CTC CTC       48
Met Asp Phe Gly Leu Ala Leu Leu Leu Ala Gly Leu Leu Gly Leu Leu
 1               5                  10                  15

CTC GGC CAG TCC CTC CAG GTG AAG CCC CTG CAG GTG GAG CCC CCG GAG       96
Leu Gly Gln Ser Leu Gln Val Lys Pro Leu Gln Val Glu Pro Pro Glu
             20                  25                  30

CCG GTG GTG GCC GTG GCC TTG GGC GCC TCG CGC CAG CTC ACC TGC CGC      144
Pro Val Val Ala Val Ala Leu Gly Ala Ser Arg Gln Leu Thr Cys Arg
         35                  40                  45

CTG GCC TGC GCG GAC CGC GGG GCC TCG GTG CAG TGG CGG GGC CTG GAC      192
Leu Ala Cys Ala Asp Arg Gly Ala Ser Val Gln Trp Arg Gly Leu Asp
     50                  55                  60

ACC AGC CTG GGC GCG GTG CAG TCG GAC ACG GGC CGC AGC GTC CTC ACC      240
Thr Ser Leu Gly Ala Val Gln Ser Asp Thr Gly Arg Ser Val Leu Thr
 65                  70                  75                  80

GTG CGC AAC GCC TCG CTG TCG GCG GCC GGG ACC CGC GTG TGC GTG GGC      288
Val Arg Asn Ala Ser Leu Ser Ala Ala Gly Thr Arg Val Cys Val Gly
                 85                  90                  95

TCC TGC GGG GGC CGC ACC TTC CAG CAC ACC GTG CAG CTC CTT GTG TAC      336
Ser Cys Gly Gly Arg Thr Phe Gln His Thr Val Gln Leu Leu Val Tyr
            100                 105                 110

GCC TTC CCG GAC CAG CTG ACC GTC TCC CCA GCA GCC CTG GTG CCT GGT      384
Ala Phe Pro Asp Gln Leu Thr Val Ser Pro Ala Ala Leu Val Pro Gly
        115                 120                 125

GAC CCG GAG GTG GCC TGT ACG GCC CAC AAA GTC ACG CCC GTG GAC CCC      432
Asp Pro Glu Val Ala Cys Thr Ala His Lys Val Thr Pro Val Asp Pro
    130                 135                 140

AAC GCG CTC TCC TTC TCC CTG CTC GTC GGG GGC CAG GAA CTG GAG GGG      480
Asn Ala Leu Ser Phe Ser Leu Leu Val Gly Gly Gln Glu Leu Glu Gly
```

```
                       145                 150                 155                 160
GCG CAA GCC CTG GGC CCG GAG GTG CAG GAG GAG GAG GAG CCC CAG                        528
Ala Gln Ala Leu Gly Pro Glu Val Gln Glu Glu Glu Glu Pro Gln
                165                 170                 175

GGG GAC GAG GAC GTG CTG TTC AGG GTG ACA GAG CGC TGG CGG CTG CCG                    576
Gly Asp Glu Asp Val Leu Phe Arg Val Thr Glu Arg Trp Arg Leu Pro
                    180                 185                 190

CCC CTG GGG ACC CCT GTC CCG CCC GCC CTC TAC TGC CAG GCC ACG ATG                    624
Pro Leu Gly Thr Pro Val Pro Pro Ala Leu Tyr Cys Gln Ala Thr Met
                195                 200                 205

AGG CTG CCT GGC TTG GAG CTC AGC CAC CGC CAG GCC ATC CCC GTC CTG                    672
Arg Leu Pro Gly Leu Glu Leu Ser His Arg Gln Ala Ile Pro Val Leu
        210                 215                 220

CAC AGC CCG ACC TCC CCG GAG CCT CCC GAC ACC ACC TCC CCG GAG TCT                    720
His Ser Pro Thr Ser Pro Glu Pro Pro Asp Thr Thr Ser Pro Glu Ser
225                 230                 235                 240

CCC GAC ACC ACC TCC CCG GAG TCT CCC GAC ACC ACC TCC CAG GAG CCT                    768
Pro Asp Thr Thr Ser Pro Glu Ser Pro Asp Thr Thr Ser Gln Glu Pro
                245                 250                 255

CCC GAC ACC ACC TCC CCG GAG CCT CCC GAC AAG ACC TCC CCG GAG CCC                    816
Pro Asp Thr Thr Ser Pro Glu Pro Pro Asp Lys Thr Ser Pro Glu Pro
                260                 265                 270

GCC CCC CAG CAG GGC TCC ACA CAC ACC CCC AGG AGC CCA GGC TCC ACC                    864
Ala Pro Gln Gln Gly Ser Thr His Thr Pro Arg Ser Pro Gly Ser Thr
            275                 280                 285

AGG ACT CGC CGC CCT GAG ATC TCC CAG GCT GGG CCC ACG CAG GGA GAA                    912
Arg Thr Arg Arg Pro Glu Ile Ser Gln Ala Gly Pro Thr Gln Gly Glu
290                 295                 300

GTG ATC CCA ACA GGC TCG TCC AAA CCT GCG GGT GAC CAG CTG CCC GCG                    960
Val Ile Pro Thr Gly Ser Ser Lys Pro Ala Gly Asp Gln Leu Pro Ala
305                 310                 315                 320

GCT CTG TGG ACC AGC AGT GCG GTG CTG GGA CTG CTG CTC CTG GCC TTG                   1008
Ala Leu Trp Thr Ser Ser Ala Val Leu Gly Leu Leu Leu Leu Ala Leu
                325                 330                 335

CCC ACC TAT CAC CTC TGG AAA CGC TGC CGG CAC CTG GCT GAG GAC GAC                   1056
Pro Thr Tyr His Leu Trp Lys Arg Cys Arg His Leu Ala Glu Asp Asp
            340                 345                 350

ACC CAC CCA CCA GCT TCT CTG AGG CTT CTG CCC CAG GTG TCG GCC TGG                   1104
Thr His Pro Pro Ala Ser Leu Arg Leu Leu Pro Gln Val Ser Ala Trp
        355                 360                 365

GCT GGG TTA AGG GGG ACC GGC CAG GTC GGG ATC AGC CCC TCC                           1146
Ala Gly Leu Arg Gly Thr Gly Gln Val Gly Ile Ser Pro Ser
    370                 375                 380

TGAGTGGCCA GCCTTTCCCC CTGTGAAAGC AAAATAGCTT GGACCCCTTC AAGTTGAGAA                 1206

CTGGTCAGGG CAAACCTGCC TCCCATTCTA CTCAAAGTCA TCCCTCTGTT CACAGAGATG                 1266

GATGCATGTT CTGATTGCCT CTTTGGAGAA GCTCATCAGA AACTCAAAAG AAGGCCACTG                 1326

TTTGTCTCAC CTACCCATGA CCTGAAGCCC CTCCCTGAGT GGTCCCCACC TTTCTGGACG                 1386

GAACCACGTA CTTTTTACAT ACATTGATTC ATGTCTCACG TCTCCCTAAA AATGCGTAAG                 1446

ACCAAGCTGT GCCCTGACCA CCCTGGGCCC CTGTCGTCAG GACCTCCTGA GGCTTTGGCA                 1506

AATAAACCTC CTAAAATGAA AAAAAAAAA AAA                                               1539

(2) INFORMATION FOR SEQ ID NO:70:

(i) SEQUENCE CHARACTERISTICS:
             (A) LENGTH: 382 amino acids
             (B) TYPE: amino acid
             (D) TOPOLOGY: linear
```

(ii) MOLECULE TYPE: protein (xi) SEQUENCE DESCRIPTION: SEQ ID NO:70:

```
Met Asp Phe Gly Leu Ala Leu Leu Leu Ala Gly Leu Gly Leu Leu
 1               5                  10                  15

Leu Gly Gln Ser Leu Gln Val Lys Pro Leu Gln Val Glu Pro Glu
                20                  25                  30

Pro Val Val Ala Val Ala Leu Gly Ala Ser Arg Gln Leu Thr Cys Arg
            35                  40                  45

Leu Ala Cys Ala Asp Arg Gly Ala Ser Val Gln Trp Arg Gly Leu Asp
     50                  55                  60

Thr Ser Leu Gly Ala Val Gln Ser Asp Thr Gly Arg Ser Val Leu Thr
 65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
                100                 105                 110

Ala Phe Pro Asp Gln Leu Thr Val Ser Pro Ala Ala Leu Val Pro Gly
        115                 120                 125

Asp Pro Glu Val Ala Cys Thr Ala His Lys Val Thr Pro Val Asp Pro
    130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255

Pro Asp Thr Thr Ser Pro Glu Pro Pro Asp Lys Thr Ser Pro Glu Pro
            260                 265                 270

Ala Pro Gln Gln Gly Ser Thr His Thr Pro Arg Ser Pro Gly Ser Thr
        275                 280                 285

Arg Thr Arg Arg Pro Glu Ile Ser Gln Ala Gly Pro Thr Gln Gly Glu
    290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Ala Leu
                325                 330                 335

Pro Thr Tyr His Leu Trp Lys Arg Cys Arg His Leu Ala Glu Asp Asp
            340                 345                 350

Thr His Pro Pro Ala Ser Leu Arg Leu Leu Pro Gln Val Ser Ala Trp
        355                 360                 365

Ala Gly Leu Arg Gly Thr Gly Gln Val Gly Ile Ser Pro Ser
    370                 375                 380
```